United States Patent
Kropp et al.

(10) Patent No.: US 7,507,422 B2
(45) Date of Patent: *Mar. 24, 2009

(54) URINARY TRACT TISSUE GRAFT COMPOSITIONS AND METHODS FOR PRODUCING SAME

(75) Inventors: Bradley P. Kropp, Edmond, OK (US);
Yuan Yuan Zhang, Edmond, OK (US);
Earl Y. Cheng, Elmhurst, IL (US);
Hsueh-Kung Lin, Edmond, OK (US);
Rick Cowan, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 390 days.

This patent is subject to a terminal disclaimer.

(21) Appl. No.: 11/326,533

(22) Filed: Jan. 5, 2006

(65) Prior Publication Data
US 2006/0105054 A1    May 18, 2006

Related U.S. Application Data

(60) Division of application No. 10/314,799, filed on Dec. 6, 2002, now Pat. No. 7,078,033, which is a continuation-in-part of application No. 10/013,270, filed on Dec. 10, 2001, now Pat. No. 7,122,200.

(60) Provisional application No. 60/338,608, filed on Dec. 7, 2001.

(51) Int. Cl.
*A61K 35/38* (2006.01)
(52) U.S. Cl. ............... 424/551; 424/422; 424/484; 435/1.1
(58) Field of Classification Search ............... None
See application file for complete search history.

(56) References Cited

U.S. PATENT DOCUMENTS

| | | | |
|---|---|---|---|
| 5,695,998 | A | 12/1997 | Badylak et al. |
| 5,762,966 | A | 6/1998 | Knapp, Jr. et al. |
| 5,866,414 | A | 2/1999 | Badylak et al. |
| 6,576,265 | B1 | 6/2003 | Spievack |
| 2002/0087214 | A1 | 7/2002 | Kropp et al. |
| 2002/0155096 | A1 | 10/2002 | Chancellor et al. |
| 2003/0216811 | A1 | 11/2003 | Badylak et al. |

OTHER PUBLICATIONS

Raofi et al, Transplantation, 1999, vol. 68, No. 2, pp. 188-191.*

(Continued)

*Primary Examiner*—Leon B Lankford
*Assistant Examiner*—Allison M. Ford
(74) *Attorney, Agent, or Firm*—Dunlap Codding, P.C.

(57) ABSTRACT

A method for repairing damaged or diseased urinary tract tissue includes providing a urinary tract tissue graft composition that includes a distal ileal segment of small intestinal submucosa. The distal ileal segment of small intestinal submucosa may be utilized as an unseeded tissue graft composition, or the distal ileal segment of small intestinal submucosa may be positioned in a tissue culture frame, and smooth muscle and urothelial cells isolated from a tissue specimen of a subject and cultured are then seeded upon the distal ileal segment of small intestinal submucosa, thereby forming a urinary tract tissue graft.

6 Claims, 27 Drawing Sheets
(15 of 27 Drawing Sheet(s) Filed in Color)

OTHER PUBLICATIONS

Zhang et al.; "'Co-Culture' of Bladder Smooth Muscle And Urothelial Cells On Small Intestinal Submococa (sis): Evaluation Of The Best Culture Method For In Vitro Tissue Engineering Techniques"; Pediatrics Journal Supp: Sep. 1999:807-808.

Lu et al.; "Muscle-Derived Stem Cells Seeded Into Acellular Scaffolds Develop Calcium-Dependent Contractile Activity That Is Modulated By Nicotinic Receptors"; Urology 61:1285-1291, 2003.

* cited by examiner

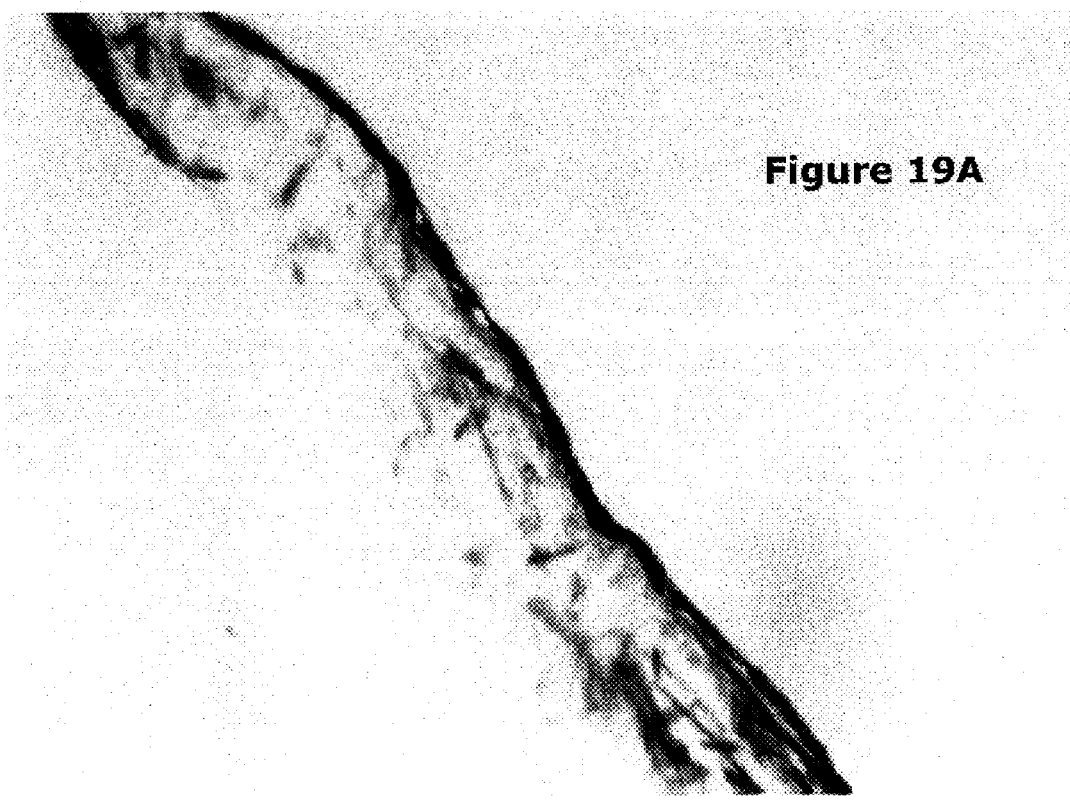

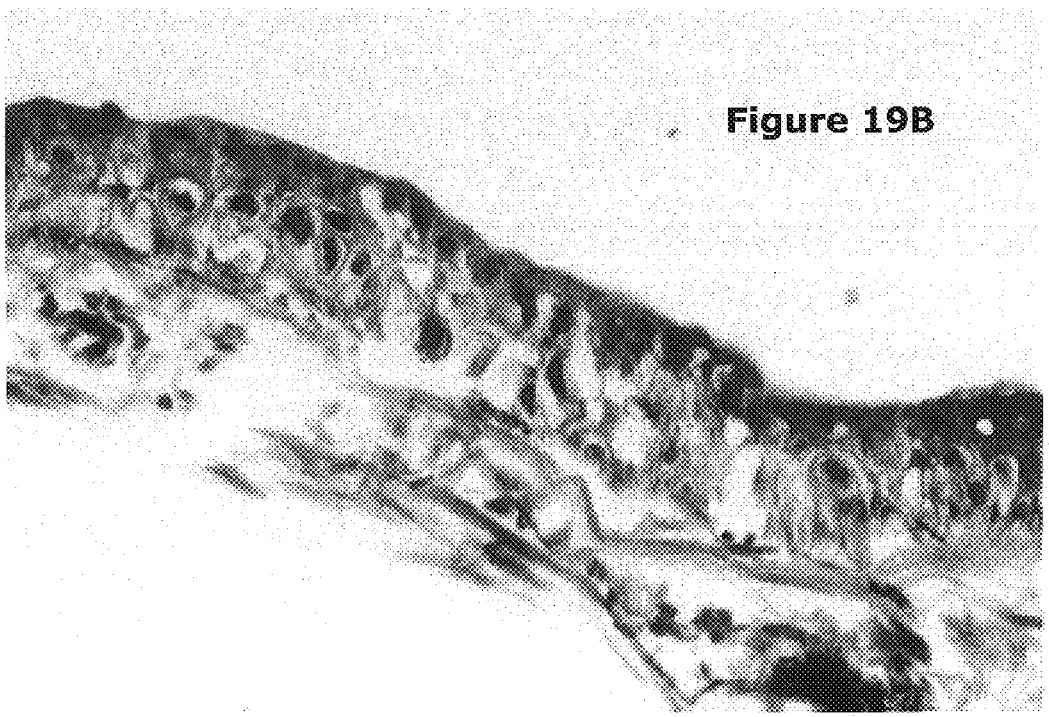

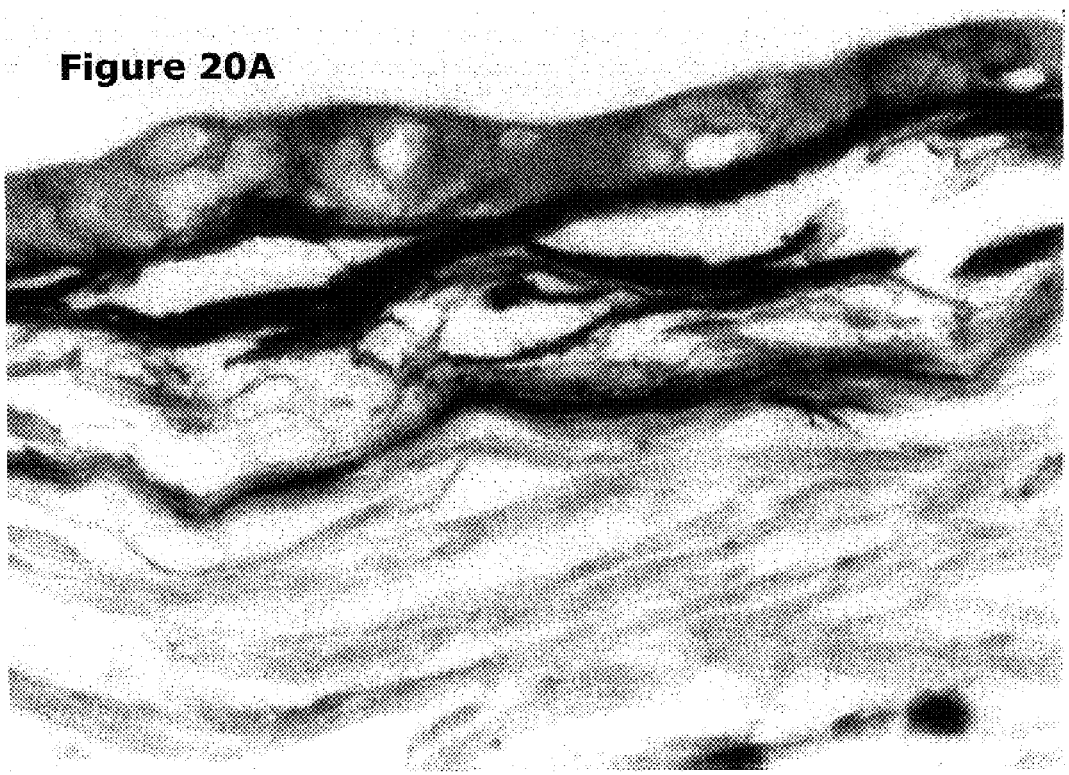

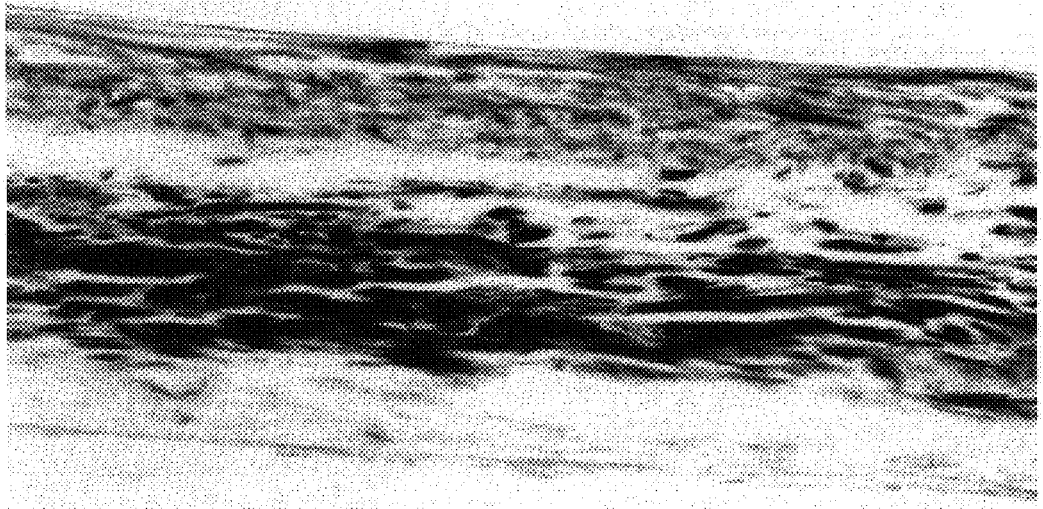

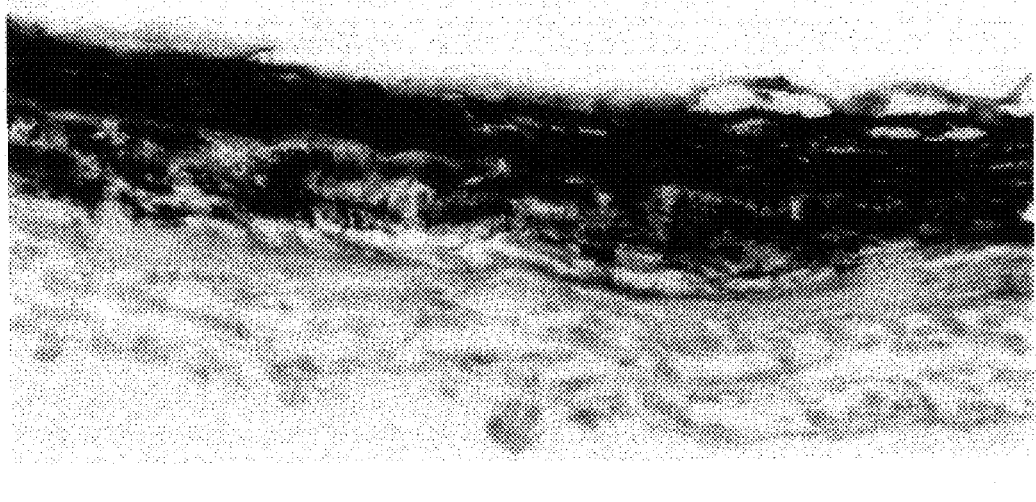

URINARY TRACT TISSUE GRAFT COMPOSITIONS AND METHODS FOR PRODUCING SAME

CROSS-REFERENCE TO RELATED APPLICATIONS

This application is a divisional of U.S. Ser. No. 10/314,799, filed Dec. 6, 2002 now U.S. Pat. No. 7,078,033; which claims the benefit under 35 U.S.C. 119(e) of U.S. Provisional Application Ser. No. 60/338,608, filed Dec. 7, 2001; the contents of each of which are hereby expressly incorporated by reference herein in their entirety.

Said application Ser. No. 10/314,799 is also a continuation-in-part of U.S. Ser. No. 10/013,270, filed Dec. 10, 2001, now U.S. Pat. No. 7,122,200, the contents of which are hereby expressly incorporated by reference herein in their entirety.

FEDERALLY SPONSORED RESEARCH OR DEVELOPMENT

This application was supported in part by National Research Grants 1RO1DK56968-01A1 (Principal Investigator H. K. Lin) and 1RO1-CA90744-01 (Principal Investigator H. K. Lin) from the National Institutes of Health. The United States Government may have rights in and to this application by virtue of this funding.

BACKGROUND OF THE INVENTION

1. Field of the Invention

The present invention relates to methods of tissue reconstruction and repair, and more particularly, but not by way of limitation, to seeded tissue engineering techniques utilizing a tissue culture frame, as well as a tissue graft formed by such methods.

2. Brief Description of the Related Art

At least twenty-five percent of the clinical problems in pediatric urology are caused by neurologic lesions that affect lower urinary tract function. These clinical presentations are highlighted by urinary incontinence, urinary tract infections and decreased bladder compliance that leads to increased pressure transmission to the upper urinary tract which leads to subsequent renal deterioration. The monetary cost to our health care system of treating children with dysfunctional bladders runs into millions of dollars each year. Therefore, the need for bladder augmentation has increased in both the adult and pediatric population. This increased need requires surgical techniques that are clinically and socially acceptable and allow these children and adults to live a healthier and more normal life. The current methods of treatment of bladder dysfunction leave those goals largely unmet and must be improved if we hope to improve the prognosis of this large population of urology patients.

The gastrointestinal tract has been the autologous tissue source of choice for genitourinary reconstruction in both the adult and pediatric population. Deleterious side effects associated with the use of bowel include infection, intestinal obstruction, mucus production, electrolyte abnormalities, perforation and neoplasia. These potential side effects have ignited tissue engineering research involving bladder reconstruction through bladder regeneration. These endeavors have shown that there is an urgent need for the development of biodegradable materials with predictable behavior and well characterized mechanical properties that can be used as alternatives to gastrointestinal segments for bladder reconstruction. The major obstacle to advancing the field of urinary tract reconstruction and rehabilitation has been the availability of a biomaterial, either permanent or biodegradable, that will function as a suitable scaffold to allow the natural process of regeneration to occur. The ideal graft material would be replaced by the host tissue, promote the development of a structurally intact low pressure reservoir, and serve as a scaffold for the healing and regeneration of the bladder wall. If a suitable exogenous graft material was available, the need for autogenous tissue and all of the negative consequences associated with its harvest could be eliminated. Therefore, investigators continue to search for the proper scaffold and methodology that is necessary to regenerate tissue and maximally restore urinary tract function. Currently, two technologies involving tissue engineering for bladder regeneration and augmentation are being investigated.

The first reconstructive technology, the in vivo or unseeded tissue engineering technique for bladder regeneration, employs xenogenic (derived from stomach, bladder and small intestine) or synthetic biodegradable, acellular matrices. Such tissue engineering technique involves the direct in vivo placement of an unseeded biodegradable material into a host that will then function as a scaffold to allow the natural process of regeneration to occur. While this technology provides the scaffold for wound healing and tissue regeneration, it also requires the host to provide the tissue and proper environment for cell growth and tissue regeneration.

There are two major obstacles for in vivo or unseeded tissue engineering technology for bladder regeneration. The first has been finding a biomaterial that will act as a suitable scaffold for this natural process to occur. Synthetic non-biodegradable biomaterials such as silicone, rubber, polytetrafluoroethylene, and polypropylene have been unsuccessful because of mechanical failure, lithogenesis, or host foreign body reactions (see, e.g., Kudish, H. G., *J. Urol.* 78:232 (1957); Ashkar, L. and Heller, E., *J. Urol.* 98:91 (1967); Kelami et al., *J. Urol.* 104:693 (1970)). As a consequence of failures with non-biodegradable materials, synthetic biodegradable materials have been investigated that would allow the host bladder time for regeneration but then dissolve prior to the onset of any foreign body reaction. These materials have been applied experimentally and have shown improvement over non-biodegradable materials. Xenogenic, collagen-rich biodegradable materials such as placenta, amnion and pericardium have been used with even more encouraging experimental results than studies employing non-biodegradable synthetic materials. However, despite initial encouraging results, none of these materials have been found to be suitable for clinical use. It has been reported that bladders augmented with dura, peritoneum, placenta and fascia contract over time, and that such tissue grafts fail to promote complete bladder wall regeneration (i.e., tissue having a urine impermeable layer and a functional muscle cell layer) (Kelami, et al., *J. Urol.* 105:518 (1971)).

The second potential limitation of the unseeded tissue engineering technique for bladder regeneration is that the size of the graft may be limited to the amount of area which can be quickly invested with bladder cells from the remaining native bladder, and therefore may not be sufficient for bladder replacement. If the ratio of the size of the unseeded graft to the amount of native bladder tissue becomes too large, the ability of the animal to invest the graft with SMC and urothelial cells appears to be compromised. In the absence of quickly covering the graft with bladder cells, contraction and excess scar formation becomes a concern and poor clinical outcomes may result.

Clearly a tissue graft material is desired which is non-immunogenic, not subject to gross shrinkage after implantation, and which promotes the growth of endogenous urinary bladder tissues having a urine impermeable cell layer and a functional muscle cell layer. A collagen-based biomaterial called small intestinal submucosa (SIS) is a xenogenic membrane harvested from small intestine (such as pig small intestine) in which the tunica mucosa is mechanically removed from the inner surface, and the serosa and tunica muscularis are mechanically removed from the outer surface. This produces a thin, translucent graft (0.1 mm wall thickness) composed mainly of the submucosal layer of the intestinal wall. The submucosal layer of animal intestine has an established background in surgery as gut suture. This collagen-rich membrane has been previously shown to function well as an arterial or venous graft eliciting rapid replacement by native tissues. For example, U.S. Pat. No. 4,902,508, issued to Badylak et al. on Feb. 20, 1990, and U.S. Pat. No. 4,956,178, issued to Badylak et al. on Sep. 11, 1990, the contents of which are hereby expressly incorporated herein by reference in their entirety, describe SIS autografts and allografts prepared from the upper jejunum of a dog and used beneficially for vascular constructs.

SIS has also been shown to have excellent host compatibility and remodeling when submucosal bladder injections of minced SIS were performed in pigs (see U.S. Pat. No. 5,275,826, issued Jan. 4, 1994, to Badylak et al., the contents of which are hereby expressly incorporated herein by reference). To date, SIS has been shown to be non-immunogenic with over 1,000 cross-species transplants and direct challenge testing, demonstrating the lack of immunogenicity thereof. Additionally, SIS has been shown to contain a combination of active intrinsic growth factors, cytokines, structural proteins, glycoproteins and proteoglycans that may assist in cell migration and cell to cell interaction as well as cell growth and differentiation during the regenerative process. Based upon these highly desirable characteristics, it appears that SIS has potential as a universal tissue graft.

Initial research using SIS for urinary bladder augmentation was performed in a rat model, and SIS was shown to function as a scaffold to allow the native rat bladder to remodel and regenerate itself. Histologically, the regenerated rat bladders contained all three layers of the bladder (urothelium, smooth muscle and serosa) and were indistinguishable from normal rat bladder at 11 months post-augmentation (Kropp et al., *Urology* 46:396 (1995)). In addition, in vitro contractility studies showed that strips of in vivo tissue engineered SIS-regenerated rat bladder had contractile properties and nerve regeneration that was similar to the normal rat bladder (Vaught et al., *J. Urol.* 155:374 (1996)). This was the first evidence that a functional bladder could be achieved with tissue engineering techniques. It also demonstrated that SIS was different than other biomatrix materials that have been studied in the past. Previously, no other material had shown the ability to promote the regenerative capacity of bladder tissue that SIS was demonstrating in the small animal model.

A long term, large animal model evaluating in vivo tissue engineering of SIS bladder augmentation, in which 40% of a canine bladder was removed and replaced with a similar size piece of SIS, demonstrated that the regenerated bladder remained urodynamically compliant with similar capacities as control dogs. There were no deleterious side effects or upper tract changes up to 15 months post-augmentation. Gross examination revealed that all three layers of the bladder had regenerated. However, the quantity and organization of smooth muscle fibers differed slightly from the normal bladder (Kropp et al., *J. Urol.* 155:2098 (1996)). In vitro contractility bladder strip studies performed on the SIS-regenerated portions of the bladder demonstrated contractile activity and expression of muscarinic, adrenergic and purinergic receptors similar to normal bladder. As was the case in the rat model, SIS-regenerated bladder also demonstrated functional nerve regeneration and innervation that is similar to normal bladder. Finally, in vitro stress/strain compliance studies demonstrated no significant difference between SIS-regenerated bladder and control bladder, both of which were 30-fold more compliant than the original SIS graft material (Kropp et al., *J. Urol.* 156:599 (1996)).

Critical histological analysis of the regenerated bladder tissue has revealed that the collagen-to-muscle ratio is increased in small intestinal submucosa regenerated bladder compared to normal bladder and that the degree of regeneration is variable within a given graft. The clinical and functional implications of these findings are not clear. In addition, while the obstacle of identifying a biomaterial that will act as a suitable scaffold for the natural process of bladder regeneration to occur is overcome by the use of SIS in unseeded tissue engineering technology, the obstacle of the limited size of a graft formed therefrom still exists.

Further, while small intestinal submucosa has been shown to promote urinary bladder regeneration, in the past, all segments of the small intestine have been used for urinary bladder regeneration, and it was thought that all segments produced similar results. However, over the last few years multiple problems have been encountered with different small intestinal segments, including calcifications and graft shrinkage, and therefore unreliable and inconsistent results have been obtained in the experimental use of this material for bladder augmentation.

The second tissue reconstruction technology, the in vitro or seeded tissue engineering technique, utilizes biodegradable materials that serve as both a scaffold for the regeneration process to occur as well as cell-delivery vehicles. This technology involves initial harvesting of bladder tissue, such as from a biopsy from host native tissue, to establish primary cultures of bladder cells. Cilento et al. (*J. Urol.* 152:665 (1994)) demonstrated that it is theoretically possible to expand a transitional epithelial strain to cover the area of an entire football field using this method of cell culture. These cells are then seeded on a biodegradable membrane and, following a period of graft maturation, the in vitro created bladder graft is then transplanted back into the host for continuation of the regeneration process.

In 1992, Atala et al. (*J. Urol.* 148:658 (1992)) demonstrated the successful use of non-woven polyglycolic acid polymers (PAP) to facilitate the in vitro growth of rabbit and human bladder epithelium and smooth muscle cells. They further demonstrated that human transitional epithelium and smooth muscle cells grown on the biodegradable polymers could then be implanted into athymic mice and grown in vivo, and that the tissue architecture became progressively more complex with time in the animal.

Recently, Yoo et al. (*Urology* 51:221 (1998)) and Oberpenning et al. (*Nat. Biotechnol.* 17:149 (1999)) reported on the feasibility of dog bladder augmentation using allogenic bladder submucosa and PAP membranes seeded with urothelial and smooth muscle cells. This study demonstrated that transitional epithelium and smooth muscle cells could be harvested, grown and subsequently seeded on allogenic bladder submucosa for use as augmentation material. Urodynamically, the augmented bladder demonstrated increased capacity during this short term study. Interestingly, the allogenic bladder submucosa which was unseeded also demonstrated the ability to increase bladder capacity, however the gains in capacity were less than the seeded grafts. Studies such as this as well as those of Atala et al. suggest that prior cell seeding of large bladder grafts may be necessary to obtain the best clinical outcome following bladder augmentation. Unfortunately, although the in vitro technique of tissue engineering has been shown to be feasible for both synthetic and xenogenic matrices, thus far no studies have been undertaken to determine the effectiveness of the materials to facilitate the regeneration of functional bladder tissue in a large animal.

In addition, while all segments of small intestinal submucosa have been used to promote urinary bladder regeneration, multiple problems have been encountered with different small intestinal segments, including calcifications and graft shrinkage, and therefore unreliable and inconsistent results have been obtained in the experimental use of this material for bladder augmentation. However, thus far no studies have been undertaken to determine if the effectiveness of one segment of small intestine over another and to determine if the use of one segment of small intestine over another has any effect on the consistency and reliability of the grafts formed therefrom.

Therefore, there is a need felt within the art to identify a method of tissue engineering which will provide a large-scale, functional urinary tract tissue graft composition for consistently and reliably repairing damaged urinary tract tissue while preventing formation of calcifications and preventing any substantial reduction in graft size, thereby overcoming the disadvantages and defects of the prior art.

SUMMARY OF THE INVENTION

The present invention relates to materials for repairing or augmenting tissues and methods for using same. More particularly, the present invention is related to a method of providing a large-scale, functional urinary tract tissue graft composition, as well as the urinary tract tissue graft composition produced by such method. Broadly, the method of the present invention includes providing a tissue culture frame in which a distal ileal segment of SIS membrane is suspended and held in a taut position such that cells may be seeded thereon. The tissue culture frame allows cells seeded on the SIS, such as smooth muscle and urothelial cells, to continue to proliferate as well as mature into desired tissue sheets. The method includes isolating and culturing smooth muscle and urothelial cells from a tissue specimen of a donor. The smooth muscle cells are seeded on a mucosal surface of the SIS suspended in the tissue culture frame, followed by seeding of the urothelial cells on either a serosal surface of the SIS or upon the smooth muscle cells attached to the mucosal surface of the SIS. The tissue graft composition is then allowed to mature in culture until the smooth muscle and urothelium are maximally differentiated and assume a tissue-like phenotype, and the tissue graft composition can then be implanted back into the tissue donor.

An object of the present invention is to provide a method for providing a urinary tract tissue graft composition.

Another object of the present invention, while achieving the before-stated object, is to provide a urinary tract tissue graft composition.

Another object of the present invention, while achieving the before-stated objects, is to provide a method for repairing a damaged urinary tract tissue of a subject.

Other objects, features and advantages of the present invention will become apparent from the following detailed description when read in conjunction with the accompanying drawings and appended claims.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 19 is photomicrographs of urothelial cells grown alone on small intestinal submucosa for 28 days in low calcium conditions (A, 0.09 mM) and physiological levels of calcium (B, 2.5 mM). Urothelial cells in A demonstrate 1 to 2 layers of flattened cells (Trichrome, reduced from x63). Urothelial cells in B are cuboidal in shape and form multilayered pseudostratified urothelium (reduced from x78).

FIG. 22 is photomicrographs illustrating mixed coculture. A, at 28 days there are several layers of cells growing on top of the small intestinal submucosa with active matrix penetration of its membrane. Trichrome, reduced from x94. B, immunohistochemical analysis (urothelial cells stain red for cytokeratin AE1/AE3 and smooth muscle cells stain black for α-smooth muscle actin) shows lack of cell sorting. Reduced from x94.

DETAILED DESCRIPTION OF THE INVENTION

Figure 1:
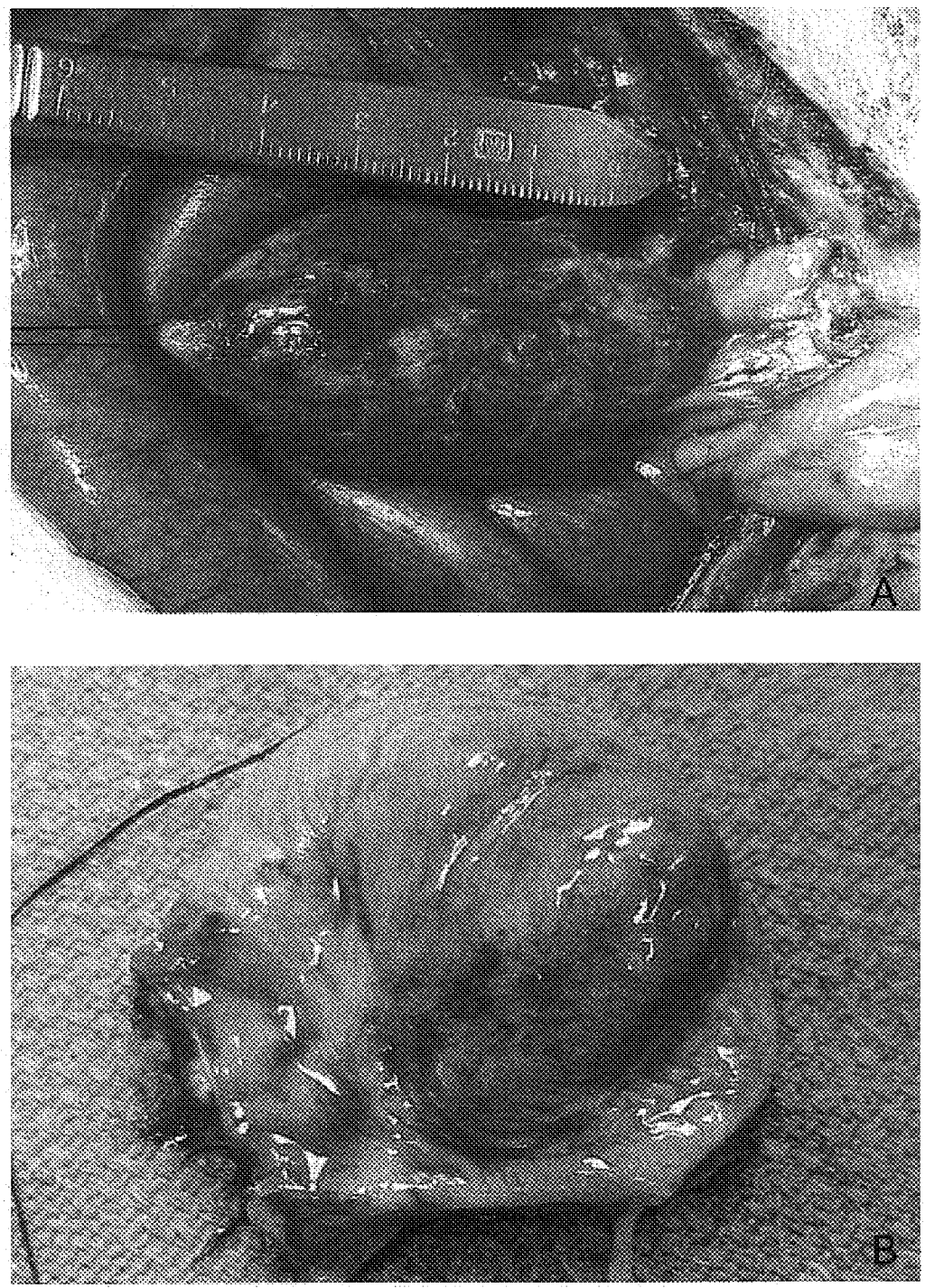
FIG. 1 are photographs of a distal SIS-regenerated bladder.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

An embodiment of the present invention is related to a method of producing a urinary tract tissue graft composition which closely resembles the architecture of normal tissue. Such urinary tract tissue graft composition comprises a xenograft of biodegradable porcine small intestinal submucosa (SIS) seeded with autologously obtained smooth muscle cells and urothelial cells to regenerate urinary tissue and restore normal urinary function. The SIS is a distal ileal segment of SIS.

The use of SIS in the method of the present invention is considered to have enhanced regenerative potential over the prior art use of PAP. SIS has been shown to have a rich supply of growth factors that have been shown in vitro to support the growth and differentiation of bladder cells. PAP lacks these factors. In addition, a much larger number of cells would be required to seed a segment of PAP compared to the same size segment of SIS. Therefore, SIS should provide a better environment and framework for the regenerative process, and therefore overcomes the defects and disadvantages of the prior art.

A nonextractable, autoclave sterilizable tissue culture frame developed for use in the SIS-supported autoaugmentation protocol for production of the urinary tract tissue graft composition of the present invention has been described in copending application U.S. Ser. No. 10/013,270, filed Dec. 10, 2001, the contents of which are hereby expressly incorporated herein by reference. In a preferred embodiment, the tissue culture frame is large enough to support a full size piece of 7×10 cm SIS membrane and can be placed into standard 150 mm tissue culture dishes for culture of tissue sheets. FIGS. 5-10 illustrate one embodiment of the tissue culture frame, wherein the tissue culture frame is a rabbet-joint frame constructed of a polymer, such as high strength clear polymethacrylate (ACRYLITE®, Idea Scientific Company, Minneapolis, Minn.). The rabbet-jointed tissue culture frame comprises two separate frame pieces, the inner frame portion and the outer frame portion. The outer frame portion is the larger of the two frame portions and has an inner rabbeted edge in which the inner frame portion snugly fits for securing of the SIS material. In the embodiment shown in FIGS. 5-10, the outer frame portion has an outer border having a length of about 11 cm and a width of about 7.5 cm and an inner border having a length of about 8.5 cm and a width of about 5.5 cm. The inner rabbeted edge extends about an additional 2 cm for placement of the inner frame portion. The inner frame portion, which does not have an aforementioned rabbeted edge, has an outer border having a length of about 8.5 cm and a width of about 5.5 cm and an inner border having a length of about 6 cm and a width of about 4.5 cm.

Shown in FIGS. 11-16 is another embodiment of a tissue culture frame which may be utilized in the method of the present invention. The tissue culture frame is constructed of a polymer, such as polypropylene, and comprises a matched set of 3 mm thick rectangular pieces (an upper frame portion and a lower frame portion) which have an outer dimension of 9×12 cm with an inner window of 6×9 cm removed. The tissue culture frame is equipped with eight 9×2 mm stainless steel pins which are permanently affixed to the lower frame portion of the tissue culture frame. A corresponding hole of 4 mm is drilled concentrically, above the pins, in the upper frame portion of the tissue culture frame so that when the tissue culture frame is assembled, the pins protrude above the upper frame portion by approximately 2 mm. When the tissue culture frame is assembled with an SIS membrane situated between the two frame portions and held in place by stainless steel binder clips, the pins pull the SIS membrane taut and hold the necessary tension on the SIS membrane which is critical for the seeded cells to differentiate in long-term culture.

While each of the above-described tissue culture frames are provided with dimensions adapted for supporting a 7×10 cm piece of SIS membrane, it is to be understood that the tissue culture frames of the present invention are not limited to such dimensions but may be provided with any dimensions which allow the tissue culture frames to function in accordance with the present invention. For example, if a larger or smaller piece of SIS membrane were utilized in the method of the present invention, the dimensions of the tissue culture frames may be varied accordingly. In addition, while the tissue culture frames of the present invention have been described as being formed of polymers, it is to be understood that such tissue culture frames may be formed of any material which allow the tissue culture frames to be sterilized and to function in accordance with the present invention. For example, either of the tissue culture frames described herein above could be formed from metal.

In addition, while two embodiments of the tissue culture frame have been described herein above and in U.S. Ser. No. 10/013,270, which has previously been incorporated by reference, it is to be understood that other embodiments of the tissue culture frame may be utilized in the method of the present invention, as long as the tissue culture frame is sterilizable, will allow a segment of SIS membrane to be suspended therein and will hold such segment of SIS membrane in a taut position such that cells may be seeded thereon.

The method of the present invention involves isolation and culture of smooth muscle and urothelial cells, such as bladder smooth muscle cells (BSMCs) and bladder urothelial cells (BUCs), from a biopsy specimen by collagenase digestion of the tissues. That is followed by seeding smooth muscle cells at a density of $1 \times 10^5$ cells/cm$^2$ on a mucosal surface of the distal ileal segment of SIS membrane which is suspended, under tension, between the frame portions of the tissue culture frame for one hour. Following the one hour period, the tissue culture frame and SIS membrane are turned over, and urothelial cells are seeded at an equal density on a serosal surface of the SIS membrane. An alternate protocol is to seed the smooth muscle cells on the mucosal surface of the SIS sheet and following a one hour period for the cells to attach to the membrane, the urothelial cells are seeded upon the attached smooth muscle cells. In both cases, the graft is then allowed to mature for 14 days in culture. At that point, smooth muscle and urothelium are maximally differentiated and are ready to be implanted back into the tissue donor.

While the urinary tract tissue graft composition described in Example 2 below is formed from bladder cells, it is to be understood that the smooth muscle cells and urothelial cells of the urinary tract tissue graft composition of the present invention may be obtained from any urinary tract tissue, including but not limited to, ureter, urethra, and tunica albuginea.

The present invention further includes a method for repairing a damaged or diseased urinary tract tissue of a subject utilizing the tissue culture frame described herein. The method involves isolating and culturing smooth muscle and urothelial cells from a urinary tract tissue specimen of a subject to provide primary cell cultures. The smooth muscle cells are first seeded on a mucosal surface of a distal ileal segment of small intestinal submucosa which is positioned in the tissue culture frame such that the distal ileal segment of small intestinal submucosa is suspended and held in a taut position by the tissue culture frame. The urothelial cells are then seeded on a serosal surface of the distal ileal segment of small intestinal submucosa. Alternatively, the urothelial cells may be seeded on top of the smooth muscle cells attached to the mucosal surface of the distal ileal segment of small intestinal submucosa. The graft formed therefrom is then allowed to mature in culture. Then the distal ileal segment of small intestinal submucosa is removed from the tissue culture frame and contacted with the damaged urinary tract tissue under conditions such that growth of the urinary tract tissue occurs and the damaged urinary tract tissue is repaired, thereby restoring urological function.

Contemporary attempts to use tissue engineering techniques to create tissue for grafting have relied on the use of synthetic matrices as a scaffold on which to seed cells. A significant disadvantage to this approach is the vast quantity of cells which must be obtained to seed the membrane due to low seeding efficiency. The low levels of cell seeding efficiency greatly reduces the utility of the approach. The procedure to isolate sufficient quantities of cells is very invasive and carries an increased risk of surgical complication.

The novelty of the method of the present invention is readily apparent when viewed in light of traditional attempts to generate functional urinary tissue where little or none had previously existed. Traditional treatment requires two significant surgical procedures, resection of the bowel and subsequent use of the autograft to augment the size of the bladder. Each procedure is associated with a significant risk of complications. We have demonstrated that enough tissue is obtained from a moderately invasive uroscopic biopsy to isolate a sufficient quantity of cells to seed the membrane in preparation for grafting. The tissue culture frame utilized in the method of the present invention allows the cells to continue to proliferate as well as mature into the desired tissue sheets. Therefore, by using the method of the present invention, the overall trauma of the process of bladder augmentation is reduced by approximately 50%. Further, the risk of stone formation and malignancy in the regenerated bladder is significantly reduced.

In yet another embodiment fo the present invention, a urinary tract tissue graft composition is provided, as well as a method for producing same. The urinary tract tissue graft composition comprises a distal ileal segment of SIS isolated from a mature adult pig. The term "distal ileal segment of SIS" is defined herein as a segment of small intestinal submucosa selected solely from the distal segment of the ileum and wherein the distal ileal segment has been isolated away from the duodenum, the jejunum and the proximal ileum of the small intestine, and wherein the distal segment was located within about 300 cm of the terminal ileum and closely associated with Peyer's patches, although Peyer's patches were not included in the segment. The urinary tract tissue graft composition described above may be utilized in a method of repairing a damaged or diseased urinary tract tissue by promoting growth of endogenous urinary tract tissues having a urine impermeable layer and a functional muscle layer. The method includes surgically removing the damaged or diseased portion of urinary tract tissue and replacing the removed portion of urinary tract tissue with the tissue graft composition described above, and wherein replacing the removed portion of urinary tract tissue with the tissue graft composition results in promotion of growth of endogenous urinary tract tissues while reducing the possibility of calcifications or stone formations as well as preventing any substantial reduction in graft size.

The following examples illustrate the practice of the preferred embodiments of the present invention. However, the present invention is not limited to the examples set forth.

EXAMPLE 1

Materials and Methods

Isolation of Distal Ileal Segment of SIS.

The entire small intestine of a pig greater than three years of age (i.e., a sow) was obtained, and the terminal ileum was identified. The bowel was then throroughly cleansed with water. The cleansed bowel was opened on the antimesenteric borders, and the terminal portion of the bowel was inspected. There were clear areas of Peyer's patches, and the areas just adjacent to Peyer's patches were used. These areas were thoroughly stripped of muocsa using a gauze sponge and mechanical force. The serosa muscle layers were also stripped using a gauze sponge and mechanical abrasion. The remaining submucosa layer of the small intestine was placed in 0.1% paracetic acid and 20% ethanol for twelve to twenty-four hours. The material was then thoroughly rinsed and placed in sterile water. Only bowel that was within 300 cm of the terminal ileum and only bowel that was closely associated with Peyer's patches was utilized. Peyer's patches were not included in the material itself.

Animal Operation

Using the canine subtotal cystectomy model, animals underwent urinary bladder augmentations with unseeded proximal or distal SIS grafts as described herein previously. Briefly, a 40% cystectomy of the dog bladder was performed, leaving the posterior plate of the bladder remaining. A single layer (0.1 mm thickness) of SIS was sutured to full thickness posterior bladder plate with water-tight running chromic suture.

The proximal and distal SIS-regenerated bladders were harvested 10 weeks after augmentation and fixed in 10% neutral buffered formalin over 24 hours. The tissue samples were studied with hematoxylin-eosin and immunohistochemical staining.

Results/Discussion

Small intestinal submucosa has been shown to promote urinary bladder regeneration. In the past, all segments of the small intestine have been used for urinary bladder regeneration, and it was thought that all segments produced similar results. However, over the last few years multiple problems have been encountered with different small intestinal segments, including calcifications and graft shrinkage, and therefore unreliable and inconsistent results have been obtained in the experimental use of this material

TABLE II

Study on Proximal v. Distal Portion SIS, 10-Week Grafts in Dogs
(Post-Op evaluations 0 = worst; 2 = best)

| | Proximal Portion SIS Graft | | | Distal Portion SIS Graft | | |
| --- | --- | --- | --- | --- | --- | --- |
| | | | Dog # | | | |
| | #4028 | #3899 | #3813 | ICJ-0 | AHJ-0 | 3853 |
| | | | (Pathology #) | | | |
| | (313) | (322) | (340) | (298) | (299) | (301) |
| Grossly: | | | | | | |
| Adhesion | 1 | 1 | 1 | 1.5 | 1 | 1.5 |
| Ureter Displace | 2 | 1 | 1 | 2 | 2 | 1.5 |
| Graft Size | 1 | 1.5 | 1 | 2 | 2 | 2 |
| Softness | 2 | 1 | 1 | 2 | 2 | 2 |
| Calcification within SIS | 2 | 0 | 0 | 2 | 2 | 2 |
| Stone in Bladder | 2 | 0 (many sandy stones) | 2 | 2 | 2 | 2 |
| Microscopically: | | | | | | |
| Urothelium reg | 2 | 2 | 2 | 2 | 2 | 2 |
| SMC bundle | 1.5 | 1.5 | 1.5 | 1.5 | 2 | 2 |
| SMC reg | 1.5 | 1.5 | 1.5 | 1.5 | 2 | 2 |
| Calcification | 2 | 0 | 0 | 2 | 0 (tiny cal) | 2 |
| Neo-vascularization | 2 | 2 | 2 | 2 | 2 | 2 |

TABLE III

Study on Proximal v. Distal Portion SIS from Three Pigs
(Post-Op evaluations 0 = worst; 2 = best)

| | Pig #1 | | Pig #2 | | Pig #3 | |
| --- | --- | --- | --- | --- | --- | --- |
| | | | Dog # | | | |
| | #4961 | #4692 | #5021 | 4693 | 5024 | 5023 |
| | | | (Pathology #) | | | |
| | (427) | (424) | (429) | (430) | (426) | (431) |
| Distal from ileumcecum (cm) | 400-420 | 260-280 | 100-120 | 200-220 | 100-120 | 200-220 |
| Grossly: | | | | | | |
| Adhesion | 1.5 | 1.5 | 1.5 | 1.5 | 1.5 | 1.8 |
| Ureter Displace | 2 | 2 | 2 | 1.5 | 2 | 2 |
| Graft Size | 1.5 | 1.5 | 1 | 1.5 | 1.5 | 2 |
| Softness | 1.5 | 1.5 | 1.5 | 2 | 1.5 | 2 |

TABLE III-continued

Study on Proximal v. Distal Portion SIS from Three Pigs
(Post-Op evaluations 0 = worst; 2 = best)

| | Pig #1 | | Pig #2 Dog # | | Pig #3 | |
|---|---|---|---|---|---|---|
| | #4961 | #4692 | #5021 | 4693 | 5024 | 5023 |
| | | | (Pathology #) | | | |
| | (427) | (424) | (429) | (430) | (426) | (431) |
| Calcification within SIS | 0 (tiny cal) | 2 | 0 | 2 | 2 | 2 |
| Stone in Bladder | 0 (sandy stones) | 2 | Undigested SIS | 0 | 2 | 0 |
| Microscopically: | | | | | | |
| Urothelium reg | 2 | 2 | 2 | 2 | 2 | 2 |
| SMC bundle | 1.5 | 1.5 | 1.0 | 2 | 1.5 | 1.5 |
| SMC reg | 1.5 | 1.5 | 1.0 (poor reg) | 2 | 1.5 | 1.5 |
| Calcification | 0 (tiny cal) | 2 | 2 | 2 | 0 (tiny cal) | 2 |
| Neo-vascularization | 2 | 2 | 1.5 | 2 | 2 | 2 | for bladder augmentation. Therefore, an object of the present invention was to determine if the swine source and/or the segment of intestine were important in creating consistent and reliable urinary bladder regeneration. U.S. Pat. No. 6,206,931, issued to Cook et al. on Mar. 27, 2001, the contents of which are hereby expressly incorporated herein by reference in its entirety, states that a most preferred source of whole small intestine is harvested from "mature adult pigs weighing greater than about 450 pounds". Tables I-II demonstrate that harvesting small intestine from an older pig, that is, a sow, in conjunction with the use of the distal ileal segment of the small intestine, produces much improved bladder regeneration.

The term "distal ileal segment of SIS" is defined herein as a segment of small intestinal submucosa selected solely from the distal segment of the ileum and wherein the distal ileal segment has been isolated away from the duodenum, the jejunum and the proximal ileum of the small intestine, and wherein the distal segment was located within about 300 cm of the terminal ileum and closely associated with Peyer's patches, although Peyer's patches were not included in the segment.

Figure 2:
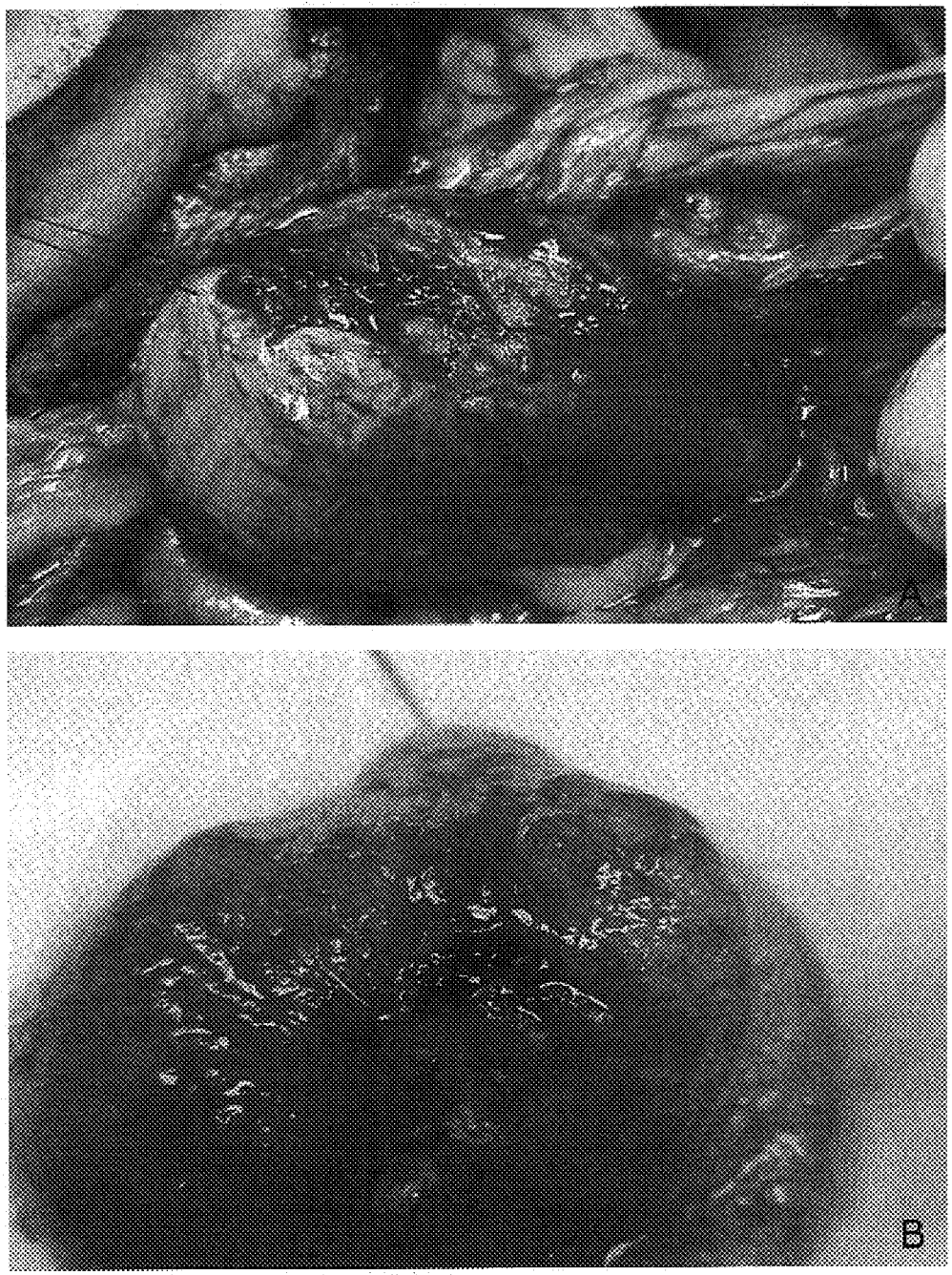
FIG. 2 are photographs of a proximal SIS-regenerated bladder.

FIGS. 1 and 2 compare the gross morphological appearance of distal SIS-regenerated bladder (FIG. 1) and proximal SIS-regenerated bladder (FIG. 2). The distal SIS-regenerated bladder has a normal spherical shape, while heavy adhesion and shrinkage are evidenced in the proximal SIS-regenerated bladder. In addition, there are less calcifications that develop within the distal SIS-regenerated urinary bladder as compared to the proximal SIS-regenerated bladder. FIG. 2B shows the formation of stones in the proximal SIS-regenerated bladder.

Figure 3:
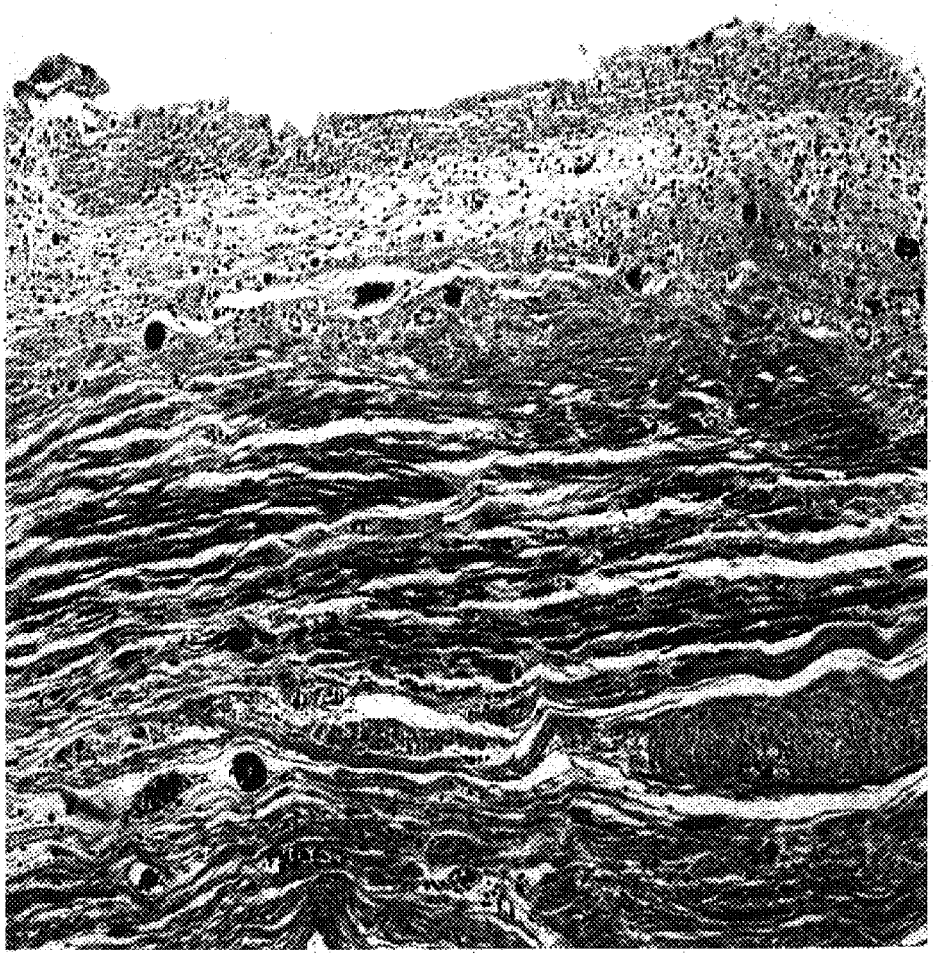
FIG. 3 is a photomicrograph of Masson trichrome stained distal SIS-regenerated dog bladder at 10 weeks postaugmentation. All layers of bladder are present. Abundant smooth muscle bundle formations (red) are surrounded by collagenous matrix (blue). ×10.
Figure 4:
FIG. 4 is a photomicrograph of Masson trichrome stained proximal SIS-regenerated dog bladder at 10 weeks postaugmentation. There is calcification formation on the mucosal layer and limited smooth muscle bundle formation among submucosa and muscle layers. ×10.
Figure 5:
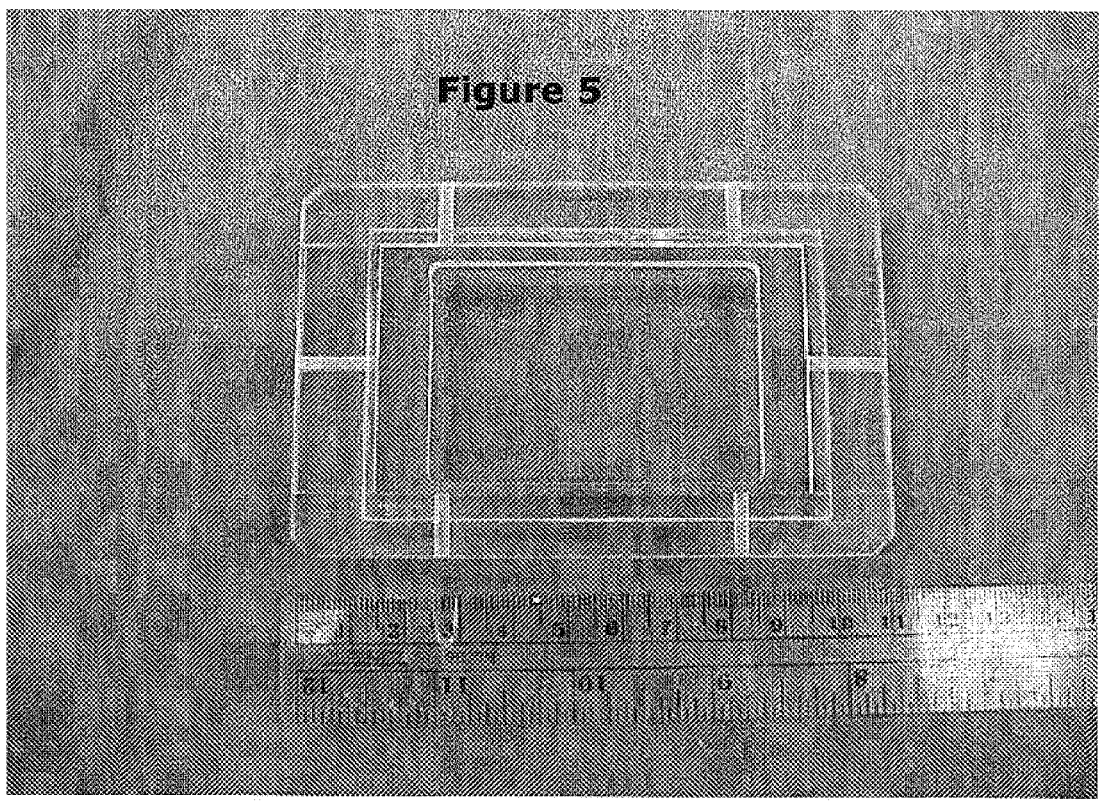
FIG. 5 is a photograph of a tissue culture frame constructed in accordance with the present invention wherein the tissue culture frame is a rabbet-jointed frame having an outer frame portion and an inner frame portion.
Figure 6:
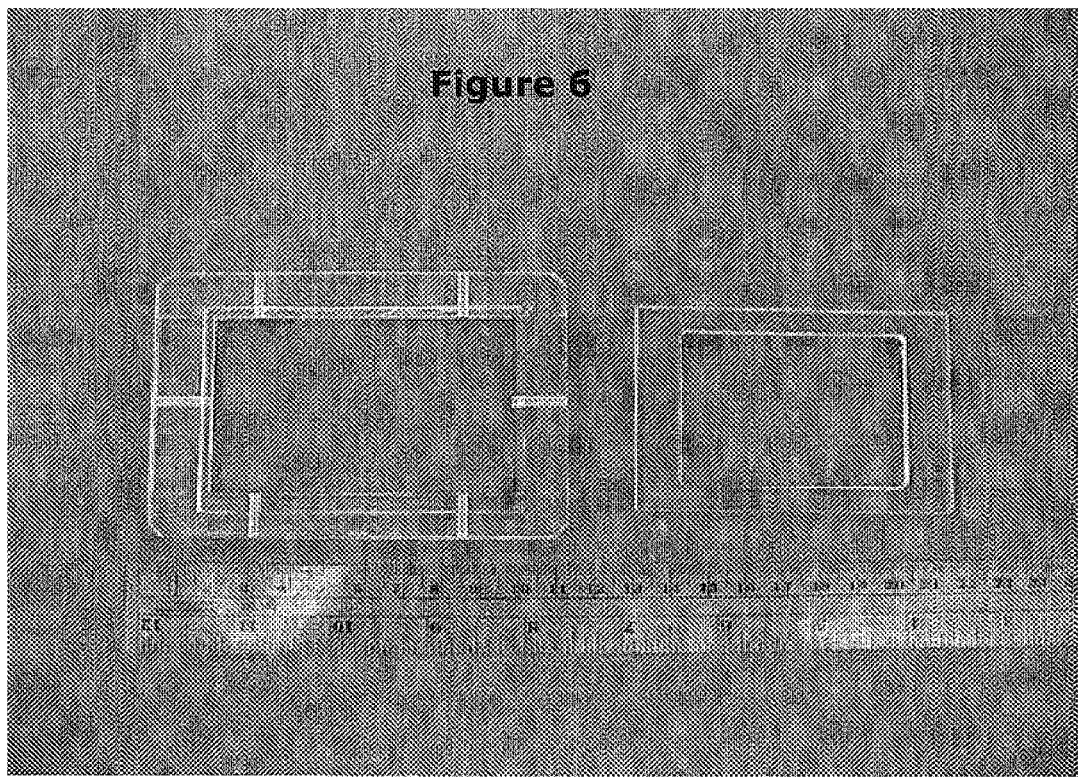
FIG. 6 is a photograph of the tissue culture frame of FIG. 5 wherein the outer frame portion and inner frame portion have been separated.
Figure 7:
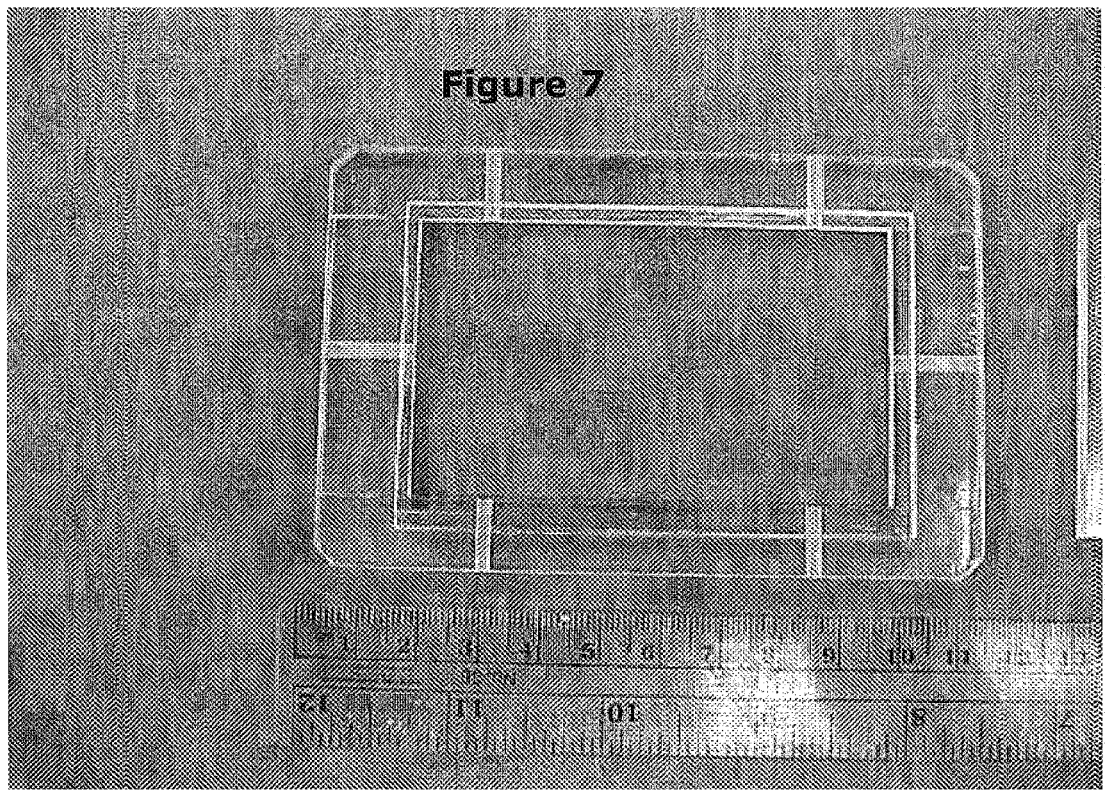
FIG. 7 is a photograph of the outer frame portion of the tissue culture frame of FIG. 5.
Figure 8:
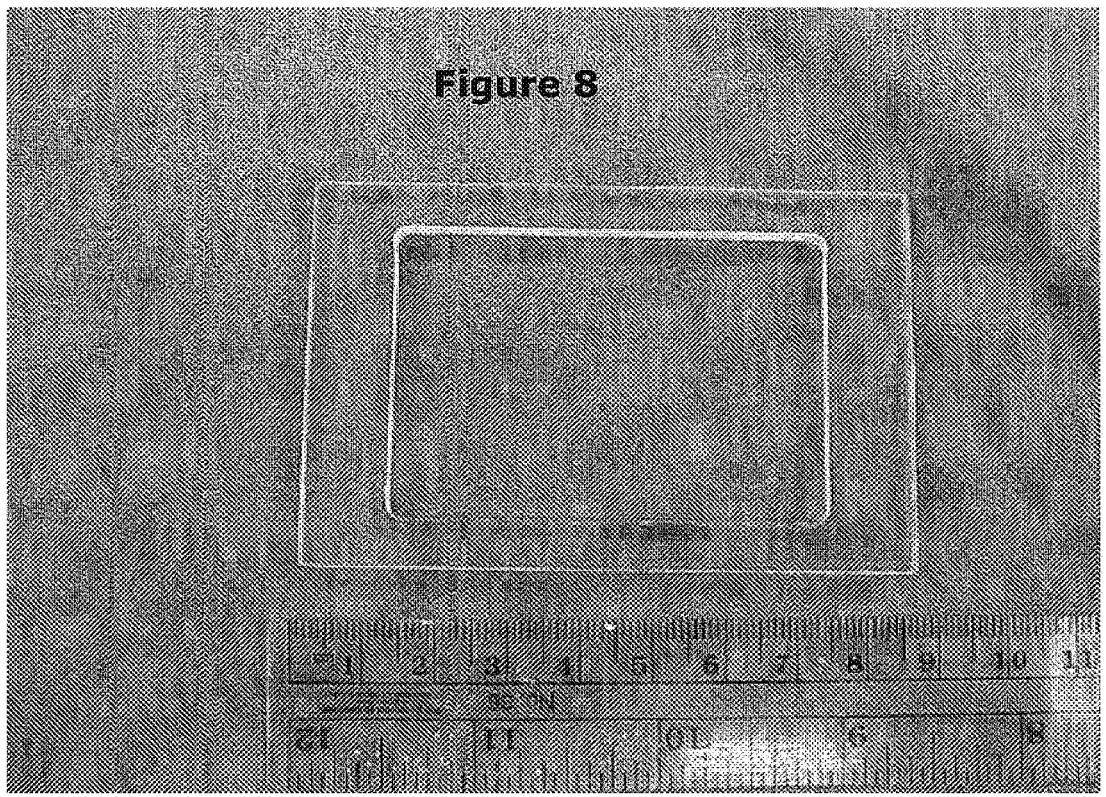
FIG. 8 is a photograph of the inner frame portion of the tissue culture frame of FIG. 5.
Figure 9:
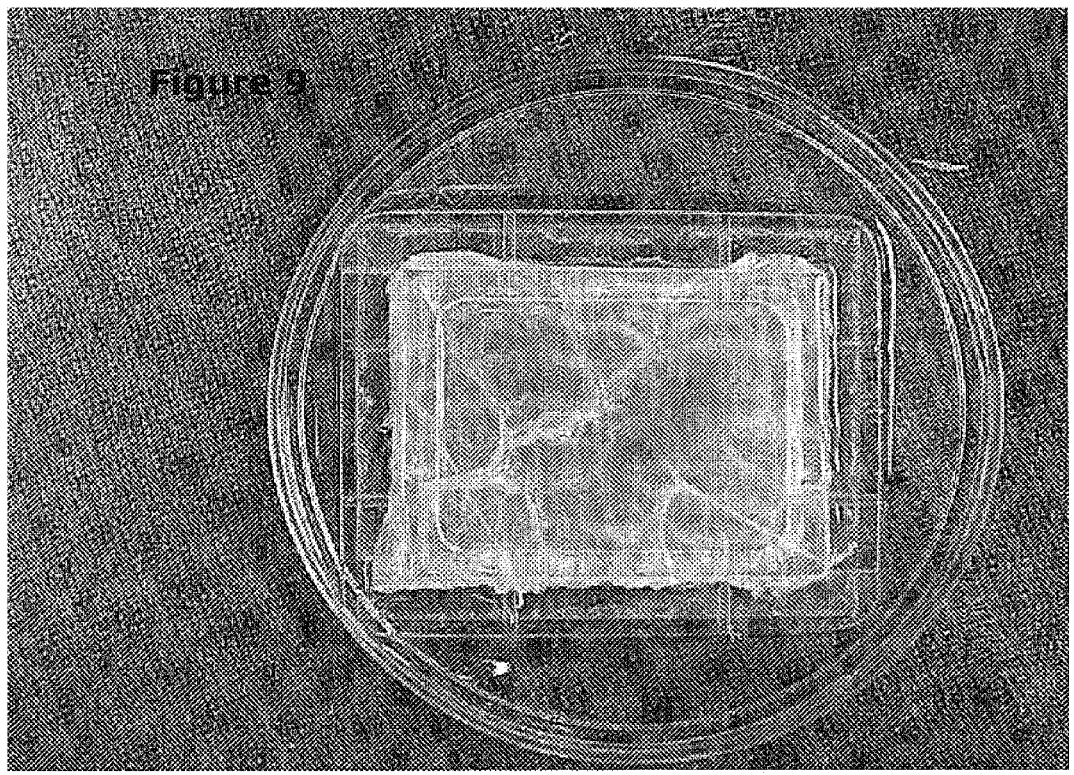
FIG. 9 is a photograph of the tissue culture frame of FIG. 5 wherein the tissue culture frame is loaded with small intestinal submucosa membrane.
Figure 10:
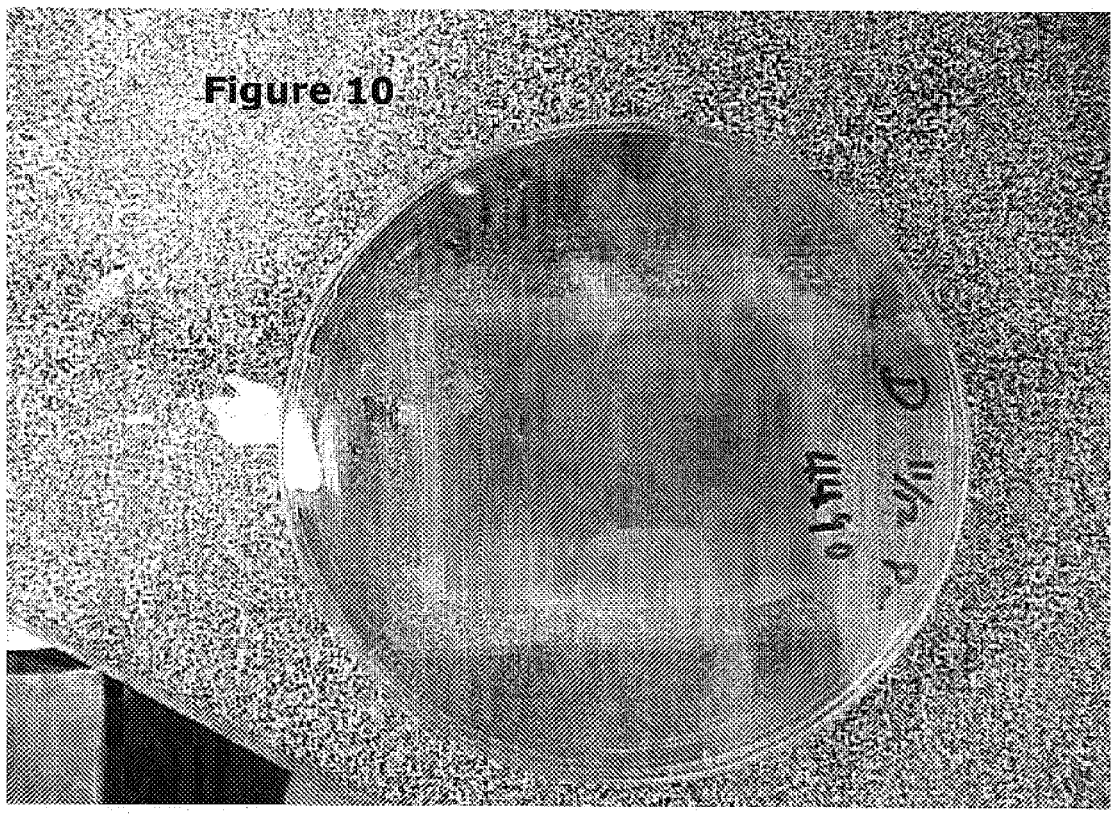
FIG. 10 is a photograph of the tissue culture frame loaded with small intestinal submucosa membrane of FIG. 9 wherein the small intestinal submucosa membrane is seeded with cells in culture medium.

FIGS. 3 and 4 are photographs of Masson's trichrome stained SIS regenerated bladder tissue using distal SIS (FIG. 3) and proximal SIS (FIG. 4). In the distal SIS-regenerated bladder (FIG. 3), all layers of bladder are present. Mild diffuse mononuclear cells infiltrate directly and are subjacent to intact normal mucosal urothelial cells. The submucosa contains areas of neovascularization. Smooth muscle bundles (red) are abundant and have a typical layered organization and are surrounded by a collagenous matrix (blue) in the smooth muscle layer. In the proximal SIS-regenerated bladder (FIG. 4), there is calcification formation on the mucosal layer and limited smooth muscle bundle formation among the submucosa and muscle layers.

Thus, several advantages exist for using the distal ileal segment of SIS: there are less calcifications and adhesions that develop within the regenerated urinary bladder, and graft shrinkage is markedly reduced when using this proper segment of SIS from an older animal. Prior to this work, it was thought that all segments of SIS were the same; however, the present invention clearly demonstrates a benefit and an improvement over pre-existing knowledge that the distal ileal segment submucosa of a mature adult pig has enhanced urinary bladder regeneration.

EXAMPLE 2

Method and Materials

Tissue Samples.

Human bladder specimens were obtained from 11 patients 2 to 11 years old with primary vesicouretal reflux undergoing open operations for ureteral reimplantation. None of the patients had clinical evidence of bladder dysfunction or neuropathic bladder. A small portion of the tissue was sent for routine histology and the remainder was used to establish primary cultures. Bladder tissue was obtained and processed in conjunction with approval from the Institutional Review Board.

Tissue samples from dog bladders were obtained from five adult male beagles (weighing between 11 and 13 kg) undergoing partial cystectomy for bladder augmentation and were used for establishing primary cell cultures. Bladder tissue was obtained and processed in conjunction with approval from the Institutional Animal Care and Use Committee.

Establishment of Primary SMC and UC Cultures.

Under the dissecting microscope the bladder mucosa was dissected off of the underlying muscle tissues using microscissors. Individual portions of mucosa and muscle tissue were then minced into fine pieces (0.5 mm$^2$) and digested with 200 units/ml collagenase IV. Individual cell suspensions were washed twice with Hank's balanced salt solution, suspended and plated on T25 PRIMARIA® cell culturing flasks. Primary cultures of urothelial cells were established in keratinocyte serum-free media (KSFM) (0.09 mM/L calcium), and SMC were cultured in modified M199 media supplemented with 10% fetal bovine serum (FBS). The cultures were incubated in a humidified 5% $CO_2$ air atmosphere at 37° C. The cells were fed with fresh media every 2 days thereafter. Once cultured urothelial cells achieved 90 to 100% confluence, they were harvested with 0.05% trypsin/EDTA and routinely passaged. Further subculturing and passaging were done in a routine fashion. Human UC and SMC used for seeding on small intestinal submucosa were between passages 2 and 8, while dog UC and SMC used for tissue culture on small intestinal submucosa were all below passage five at the time of seeding.

Small Intestinal Submucosa Disks.

Human bladder cells were seeded and grown on commercially available small intestinal submucosa disks. These 1 cm disks were manufactured in a manner such that the small intestinal submucosa is suspended over a circular polypropylene frame (border 5 mm on top and 2 mm on bottom) with the mucosal surface upward to create a double well culture disk with the small intestinal submucosa acting as the separating membrane. The mucosal surface of the small intestinal submucosa forms the base of the upward facing well while its serosal surface forms the base of the bottom well. The upper well folds 500 μl of media and the bottom well holds 200 μl. Following seeding of cells, small intestinal submucosa disks were placed in a 12 well cell culture dish filled with media to allow free contact of the media with both surfaces of the small intestinal submucosa.

Seeding of Urothelial Cells and Smooth Muscle Cells on Small Intestinal Submucosa Disks.

Figure 17:
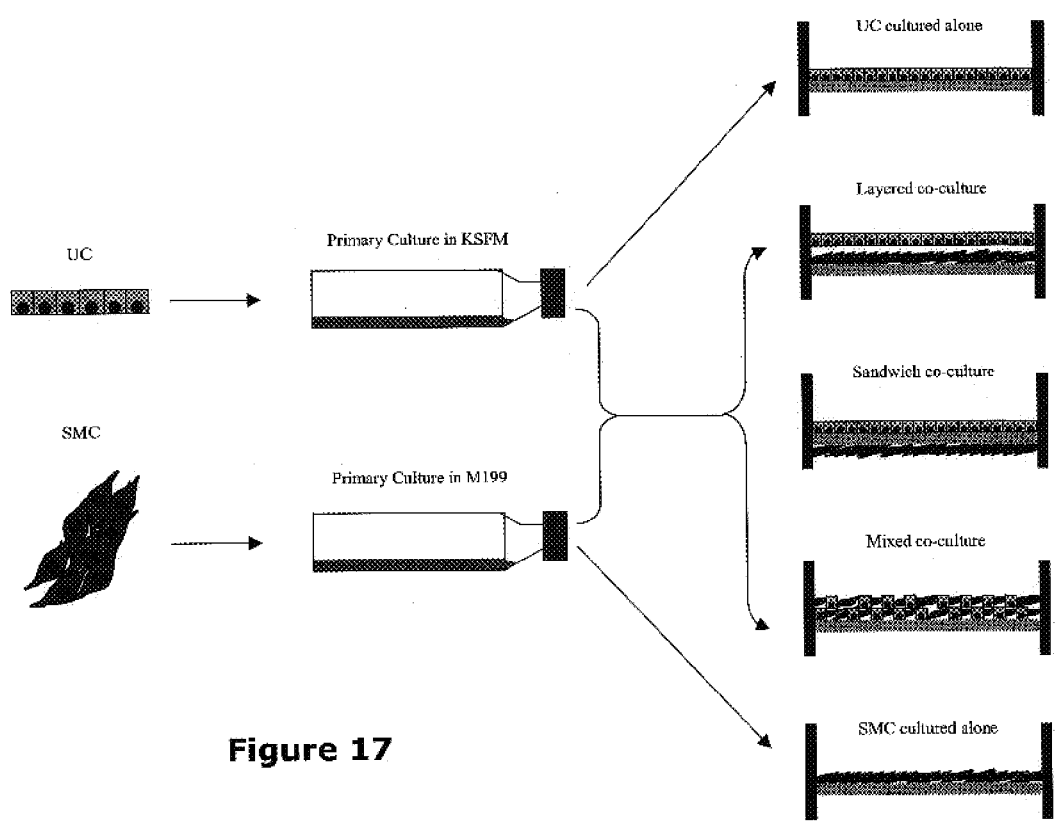
FIG. 17 is a schematic representation of the experimental design for optimizing coculture conditions. Primary cultured bladder urothelial (UC) and smooth muscle cells (SMC) were seeded alone on small intestinal submucosa or in combination with various coculture techniques. KSFM, keratinocyte serum-free media.

A diagram of the experimental design is shown in FIG. 17. Five separate groups were evaluated differing in the method of cell seeding. The first two groups were composed of urothelial cells and smooth muscle cells seeded individually on the mucosal surface of the small intestinal submucosa disks. Cells were seeded at a concentration of $10^5$ cells per cm (Kropp et al., Urology, 52:138 (1998)). To evaluate the effect of different calcium concentrations on the type of growth of urothelial cells on small intestinal submucosa, cells were maintained in keratinocyte serum-free media containing 0.09 mM and 2 mM calcium. The latter is a more physiological level of calcium that had previously been shown to support a more differentiated growth pattern of urothelial cells (Southgate et al., Lab Invest. 71:583 (1994)). Smooth muscle cells were maintained in modified M199.

The last three groups were made up of different coculture methods, which included 1 layered coculture of smooth muscle cells seeded on the mucosal surface of the small intestinal submucosa followed by seeding of urothelial cells on top of the smooth muscle cells one hour later, sandwich coculture of smooth muscle cells seeded on the serosal surface of the small intestinal submucosa disk followed by seeding of the mucosal surface with urothelial cells 24 hours later, and mixed coculture of smooth muscle cells and urothelial cells mixed together and then seeded together on the mucosal surface of the small intestinal submucosa disk. In each coculture group, cells were seeded at a density of $10^5$ cells per $cm^2$ in a medium composed on keratinocyte serum-free media and M199 mixed 1:1. Within each group cells were seeded, incubated and harvested at 3, 7, 14 and 28 days following seeding. For each separate seeding method, 3 separate disks were seeded and harvested at each time point. Once the cells were seeded on the small intestinal submucosa membrane, the medium was changed daily.

Histology and Immunohistochemistry.

At the designated time points small intestinal submucosa disks were harvested and fixed in 10% neutral buffered formalin for 24 hours. To preserve cell integrity and architecture during histological sectioning, the cell-small intestinal submucosa constructs were embedded in 4% agar and then processed for routine histology. Sections were routinely stained with hematoxylin and eosin, and Masson trichrome. To assist in identification of smooth muscle cells and urothelial cells in the coculture groups, immunohistochemical staining was performed with monoclonal antibodies to α-smooth muscle actin (1:1,000) and cytokeratin AE1/AE3 (1:100) which are specific for smooth muscle cells and urothelial cells, respectively. Cells were individually stained with α-smooth muscle actin and double stained with both antibodies using a double stain kit. Variables evaluated at each time point in each group were cell morphology, cell proliferation and layering, cell sorting, presence or absence of pseudostratified urothelium and matrix penetrance of the small intestinal submucosa membrane with smooth muscle cells.

Loading the Tissue Culture Frames with Small Intestinal Submucosa Membrane.

The intact small intestinal submucosa membrane was prepared in a standard method. Briefly, mesenteric tissue was removed from porcine jejunum. The mucosa and lamina propria of the luminal side and the serosa and external muscle layers of the abluminal side were removed mechanically. The resultant submucosa (approx. 0.2 cm thick) was rinsed extensively in water and disinfected with 0.1% peracetic acid solution and 20% ethanol for two hours.

Two types of tissue culture frames were used for preparing small intestinal submucosa membrane as a scaffold: a rabbet-joint frame (FIGS. 5-10) and a pin frame (FIGS. 11-16). The intact small intestinal submucosa membrane used for cell culture growth on either of the frames was $11 \times 7.5$ $cm^2$ in size.

1. Rabbet-Joint Tissue Culture Frame

This tissue culture frame is composed of high strength clear polymethacrylate (ACRYLITE®, Idea Scientific Company, Minneapolis, Minn.), comprising two separate frame pieces. The larger of the two frames, or outer frame, has an inner rabbet-edge in which the smaller frame, or inner frame, snugly fits for securing of the SIS material. The dimensions of the outer frame are 11 cm×7.5 cm at its outside border with the inside border being 8.5 cm×5.5 cm. The inner rabbet-edge extends an additional 2 mm for placement of the smaller frame. The smaller frame, which does not have the aforementioned rabbet-edge, has an outer dimension of 8.5 cm×5.5 cm and inner dimension of 6 cm×4.5 cm. The tissue culture frame was created by suspending small intestinal submucosa, with the luminal side up, over a rabbet-joint frame with a 5 mm tall border on top and 5 mm tall on the bottom.

2. Pinned Tissue Culture Frame

Figure 11:
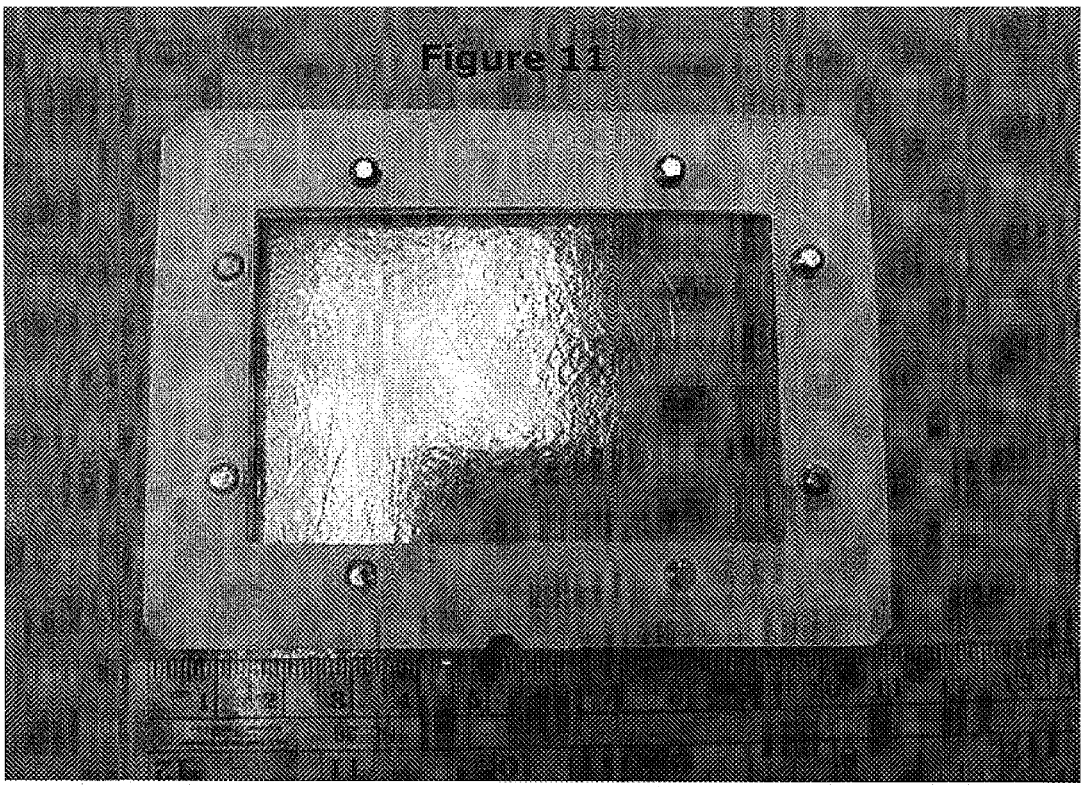
FIG. 11 is a photograph of another embodiment of a tissue culture frame constructed in accordance with the present invention wherein the tissue culture frame is a pinned frame.
Figure 12:
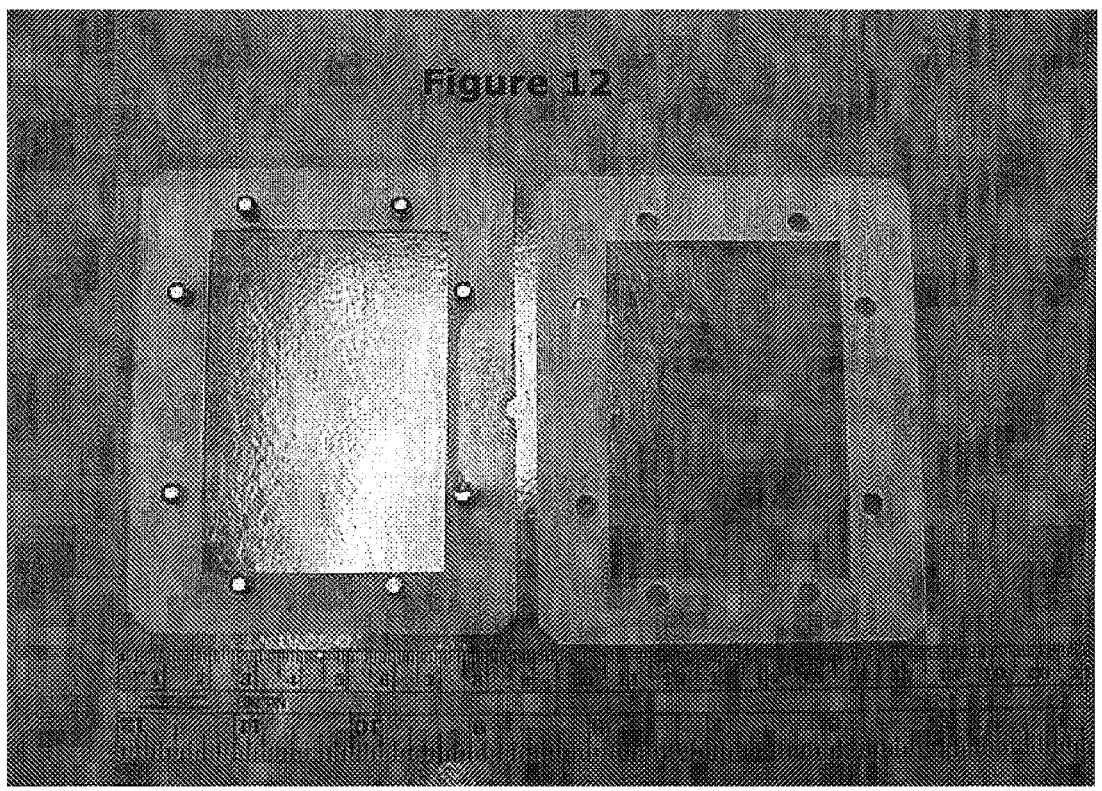
FIG. 12 is a photograph of the tissue culture frame of FIG. 11 wherein an upper frame portion and a lower frame portion of the tissue culture frame have been separated.
Figure 13:
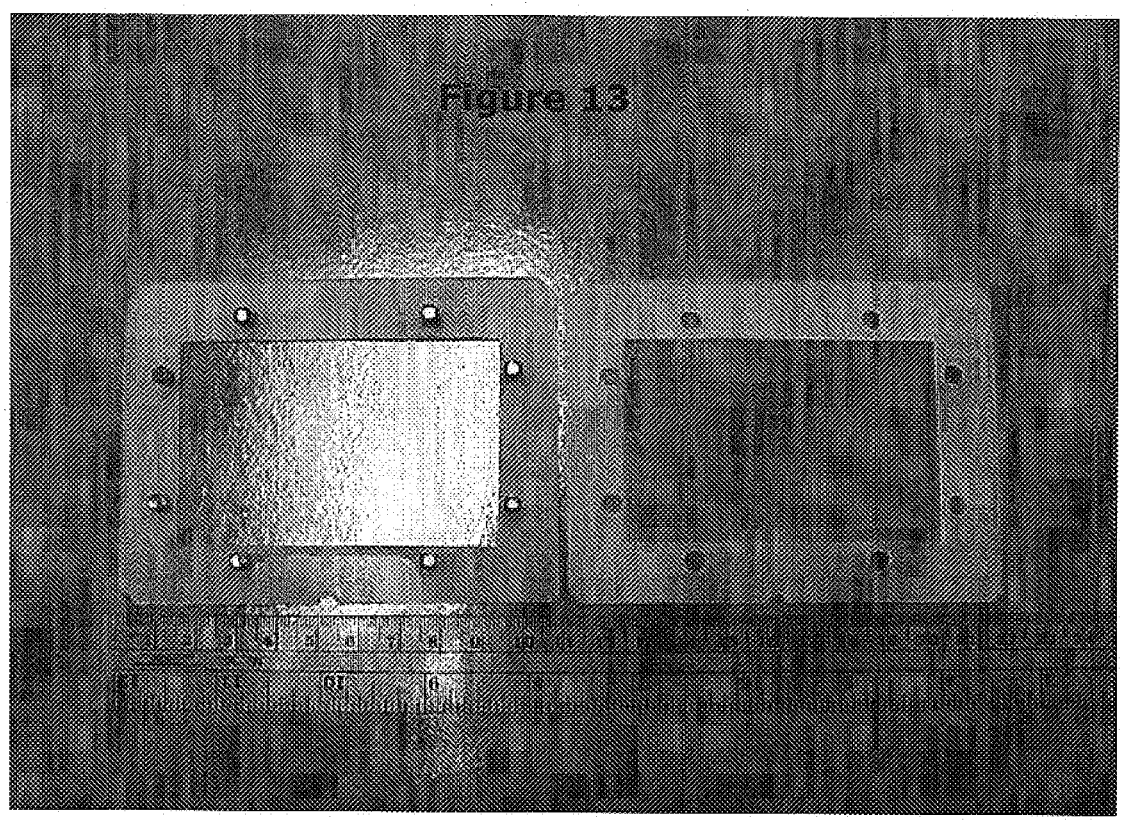
FIG. 13 is a photograph of the upper and lower frame portions of the tissue culture frame illustrated in FIG. 12 wherein the upper and lower frame portions are turned lengthwise.
Figure 14:
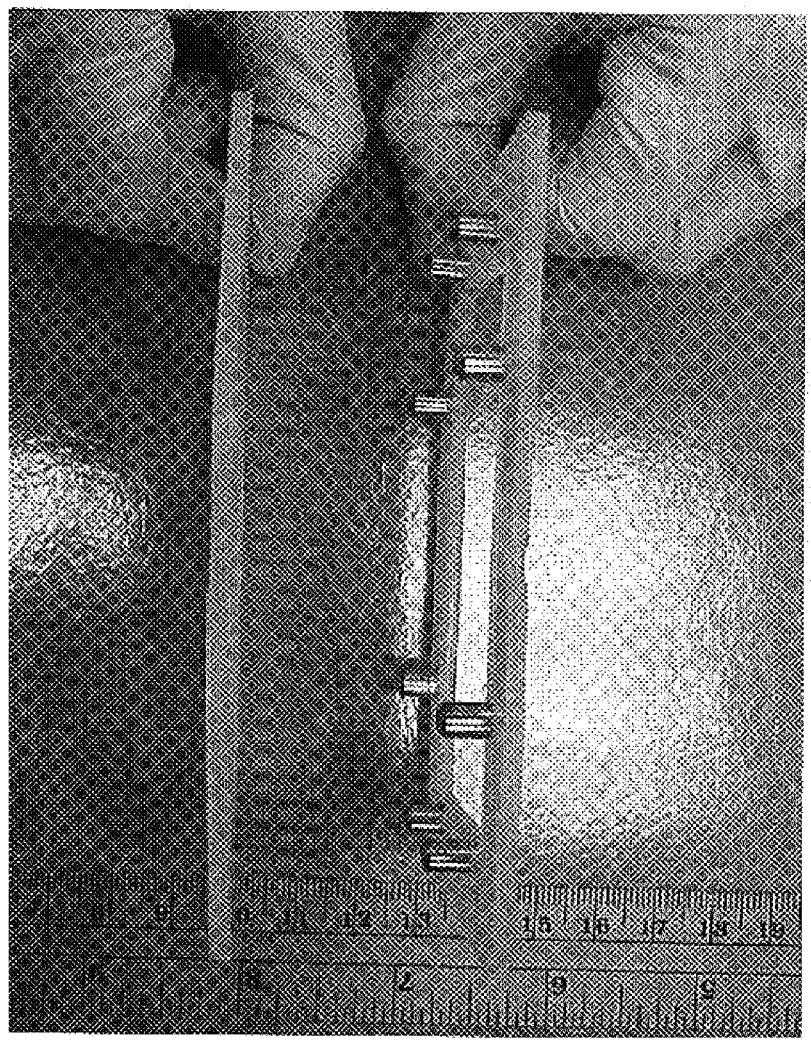
FIG. 14 is a photograph of the top plan view of the separated upper and lower frame portions of the tissue culture frame of FIG. 11.
Figure 15:
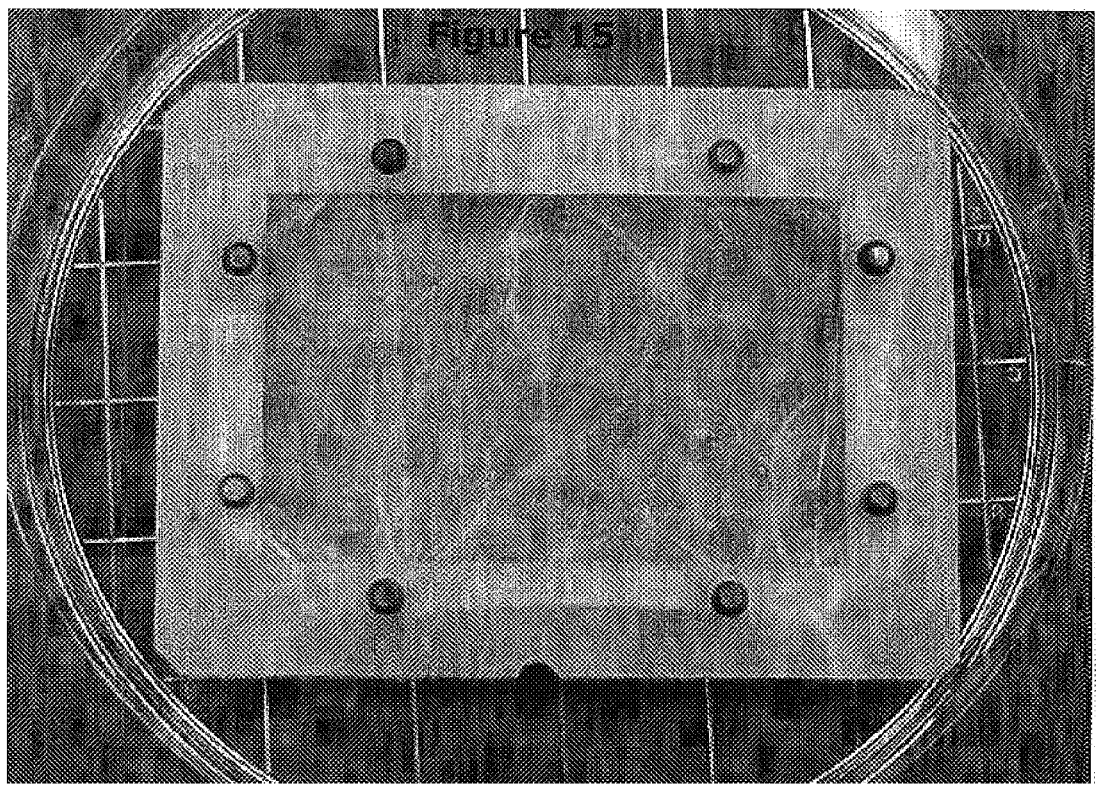
FIG. 15 is a photograph of the tissue culture frame of FIG. 11 wherein the tissue culture frame is loaded with small intestinal submucosa membrane.
Figure 16:
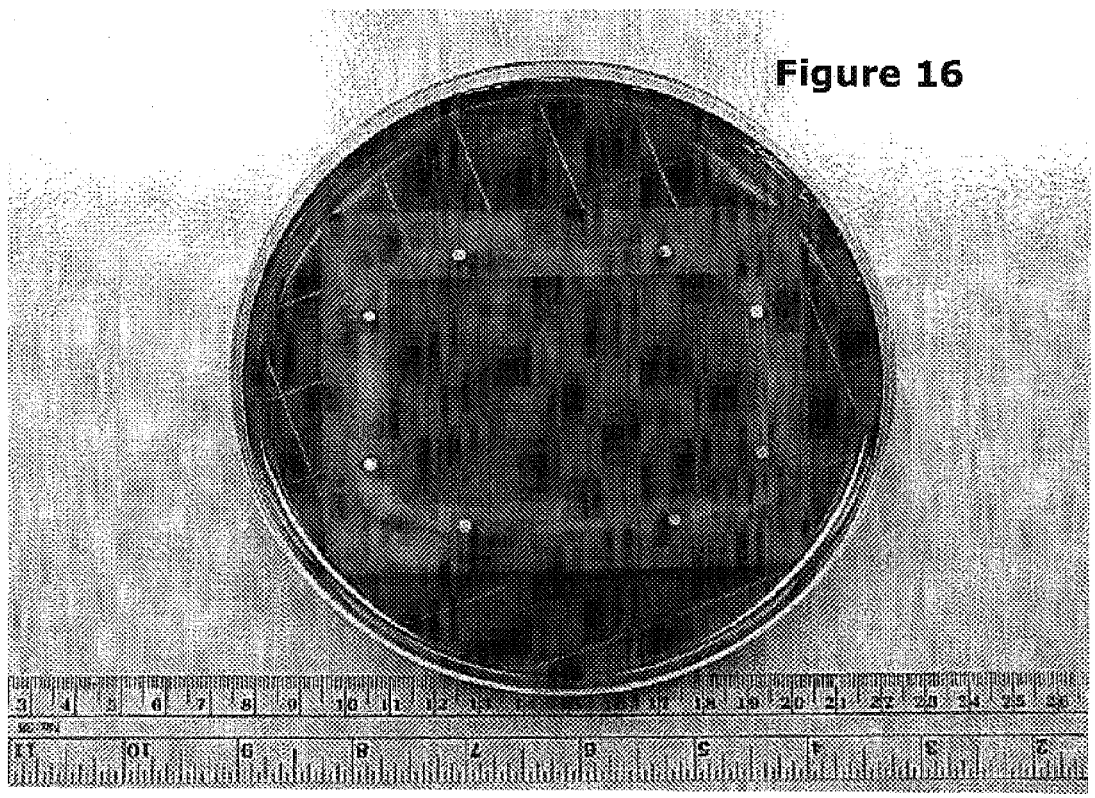
FIG. 16 is a photograph of the tissue culture frame loaded with small intestinal submucosa membrane of FIG. 15 wherein the small intestinal submucosa membrane is seeded with cells in culture medium.

The Pinned tissue culture frame (PTCF) is composed of two sheets of autoclavable polypropylene (Nalge Nunc International, Rochester, N.Y.) that are 7 cm×5 cm with a central opening of 5 cm×4 cm (see FIGS. 11 through 13). The corners are rounded off in order to allow for easier placement of the frame into a 150 mm tissue culture dish. In addition, one side of the tissue culture frame is notched to aid in aligning the top and bottom halves of the tissue culture frame after the pins have been inserted. There are eight to twelve pins located around the tissue culture frame, halfway between the outer and inner edges. The pins are composed of 5 mm surgical stainless steel and are approximately 15 mm long. The frames are placed on top of each other and holes are drilled for the pins. The pins are anchored into the bottom of the frame (via melting of the polypropylene around the pins), and the tops of the pins are rounded off. The rounding of the pin along with the large diameter prevents ripping of the Small Intestinal Submucosal membrane when putting the system together. In order to make sure that the SIS membrane stays in place during culture, four stainless steel clips are attached to each of the four sides to hold everything together (not shown).

Both of the tissue culture frames described herein above create a double-chamber with the small intestinal submucosa acting as the separating membrane. The up-well holds approximately 15 ml of media and the bottom-well holds about 20 ml. Both of the tissue culture frames were designed to provide even mechanical strains on the small intestinal submucosa membrane so that the cells are able to attach and grow on the small intestinal submucosa suspended therein.

Growth of BSMC and UC on Small Intestinal Submucosa Membranes.

Dog bladder epithelial and smooth cells were individually seeded onto the tissue culture frames with intact small intestinal submucosa membrane using coculture technique. UC were seeded on SMC layers one hour after SMC were seeded on small intestinal submucosa matrix in the mixture media of KSFM and M199 (KFSM-M199), and the cells were cultured for 14 days.

Small pieces of cell-seeded SIS grafts were cut for histological examination before being implanted back into the host animal.

Animal Operation

Using the canine subtotal cystectomy model, animals underwent urinary bladder augmentations with unseeded SIS grafts, and were directly compared to animals receiving urinary bladder augmentation with seeded SIS grafts. Using methods described in our previous study (Kropp 1998), cystometrograms (CMG), cystograms, IVU's, and serum chemistries were performed on animals pre-operatively and at 10 weeks post-implantation of the seeded or unseeded SIS to assess upper and lower urinary tract function.

The cell-seeded SIS regenerated bladders were harvested 10 weeks after augmentation and fixed in 10% neutral buffered formalin over 24 hours. The tissue samples were studied with hematoxylin-eosin and immunohistochemical staining.

Results/Discussion

A seeded graft is desired to have proliferating cells that are well attached and growing within the matrix of the biomaterial to prevent slough during the augmentation procedure, as well as to resemble normal bladder tissue. In addition, it has been shown that different biomaterials require different seeding methods for optimization of cell growth and regeneration. To determine the optimal cell seeding density, the optimal amount of time of in vitro culture post-seeding, and the best method of co culture of bladder cells to yield the best biomaterial-cell composite for placement into the host animal, human smooth muscle and urothelial cells were seeded at different densities and with different coculture methods on SIS (FIG. 17), and a number of parameters, such as cell morphology, cell adherence, cell proliferation, the development of a stratified urothelium, and the degree of smooth muscle cell invasion into the membrane, were analyzed.

Figure 18:
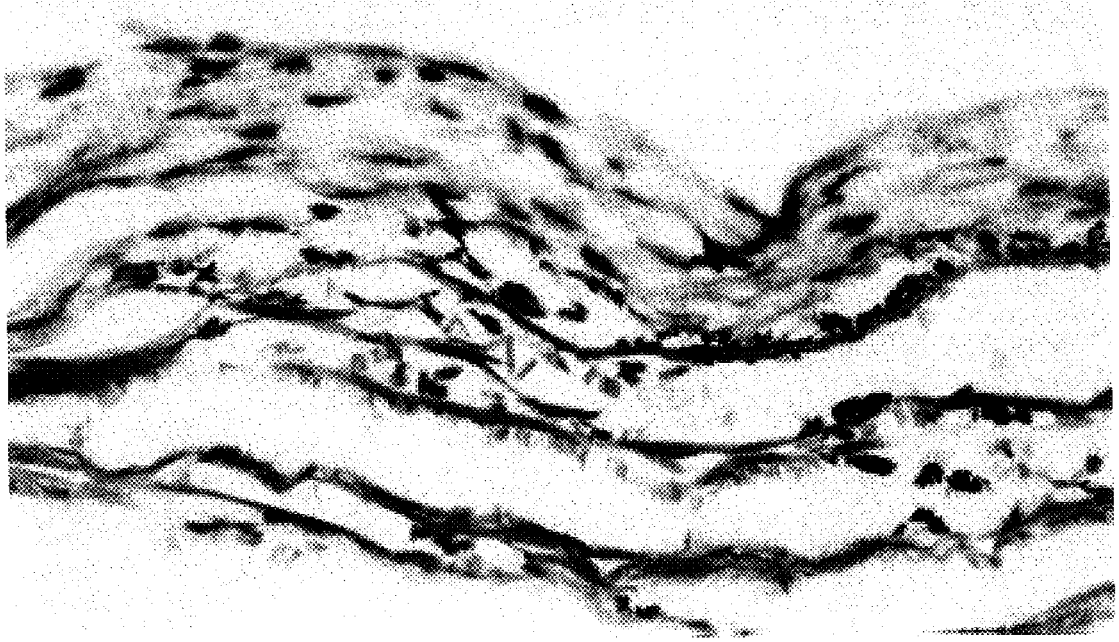
FIG. 18 is a photomicrograph illustrating smooth muscle cells grown alone on small intestinal submucosa for 28 days, which exhibit spindle shaped morphology. Cells are 5 to 7 layers thick. Majority of smooth muscle cell growth occurs on the surface of the small intestinal submucosa with areas of minimal matrix penetration just below surface. Reduced from ×94.

Primary cultures of human smooth muscle and urothelial cells were established utilizing standard explant techniques as previously described (Cilento et al., J. Urol. 152:665 (1994); Baskin et al., J. Urol. 149:190 (1993)). Bladder cells were subcultured and expanded as per routine. Smooth muscle and urothelial cells were seeded both individually and together onto intact SIS membranes (100,000-300,000 cells/membrane) and allowed to grow for up to 25 days. Cell growth on intact SIS was compared to growth on conventional plastic. Smooth muscle cells seeded onto intac SIS grew in an organized fashion in three dimensions in multiple cell layers with limited areas of matrix penetration (FIG. 18). Urothelial cells also readily adhered to SIS and grew in multiple layers (FIG. 19).

Figure 20B:
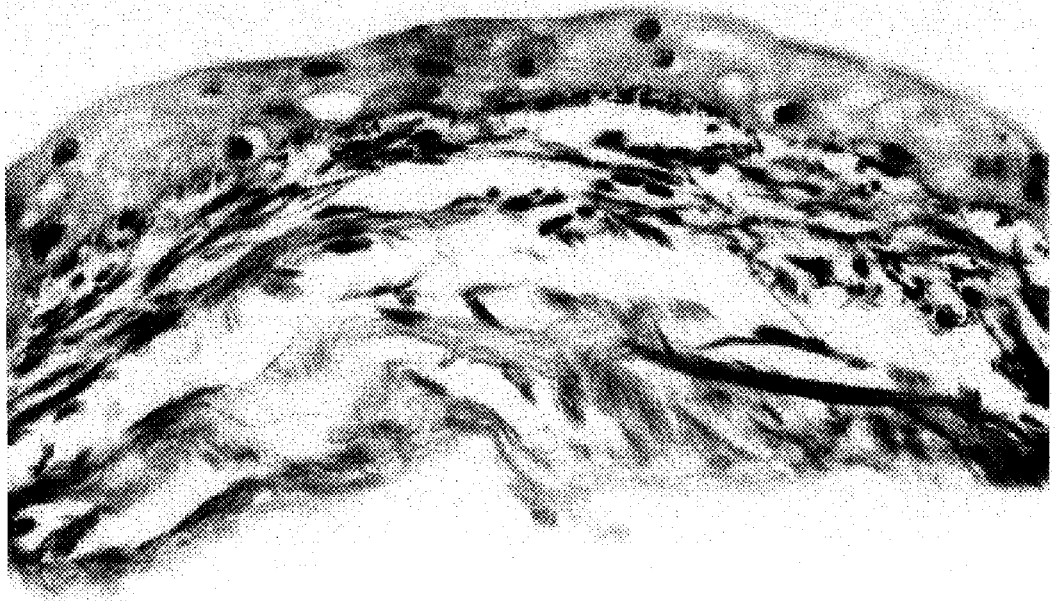
FIG. 20 is photomicrographs illustrating layered coculture. A, at 7 days there is distinct cell sorting confirmed by immunohistochemical analysis and urothelial cells (red staining for cytokeratin AE1/AE3) grow on top of smooth muscle cells (black staining for α-smooth muscle actin), that are beginning to penetrate (arrow) matrix of small intestinal submucosa membrane. Reduced from x63. B, layered coculture at 28 days reveals further development of pseudostratified layer of urothelial cells growing on top of small intestinal submucosa (open arrow). Smooth muscle cells have now penetrated matrix of small intestinal submucosa and majority of cells are below its surface (solid arrow). Note several areas where smooth muscle cells traverse deep into small intestinal submucosa membrane. This consistent pattern of matrix penetrance of small intestinal submucosa membrane by smooth muscle cells is distinctly different from minimal penetrance seen when smooth muscle cells are grown alone on small intestinal submucosa. Reduced from x94.
Figure 21:
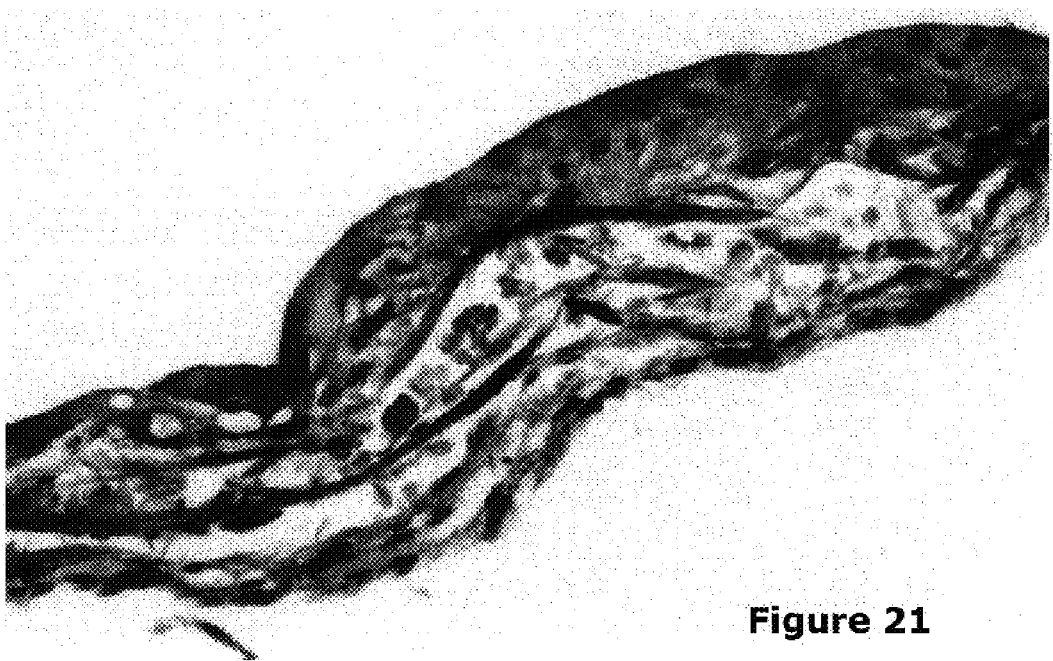
FIG. 21 is a photomicrograph illustrating sandwich coculture. At 28 days, this method shows similar growth pattern to layered coculture technique except that the urothelial cells and smooth muscle cells are on opposite sides of the small intestinal submucosa membrane. Pseudostratified layer of urothelium is on mucosal surface (open arrow) while multiple layers of smooth muscle cells are on the serosal surface and are penetrating into the matrix of the small intestinal submucosa membrane (solid arrow). Reduced from x94.

This growth pattern was distinctly different from the two-dimensional monolayer growth pattern that occurs when cells are grown on conventional plastic. When bladder smooth muscle and urothelial cells were plated together, there was a synergistic effect with regard to enhanced growth and penetration of the SIS membrane (FIGS. 20 and 21). Immunohistochemical staining patterns of smooth muscle cells ($\alpha$ smooth muscle actin and smooth muscle myosin) and epithelial cells (cytokeratin 8.12/8.13) were preserved when grown on intact SIS.

As there was no standardized method in the literature and emboldened by the success of experiments which demonstrated that it is possible to grow bladder cells on SIS in long-term tissue culture, a more thorough characterization of the culture conditions which yielded the best seeded graft on the basis of histological and immunohistochemical analysis were undertaken. Five different methods of seeding and culture were assessed at time points of 3, 7, 14 and 28 days to establish which method was most effective at developing a usable graft in the shortest period of time. We found that grafts made by sequential seeding coculture of SMC and UC (with SMC seeded on the membrane one hour prior to overseeding UC on the same surface of the membrane) for 14 days resulted in the most differentiated graft (FIG. 20). In addition, the sandwich coculture technique (FIG. 21) also resulted in organized cell sorting, formation of a well-defined pseudostratified urothelium and multilayered smooth muscle cells with enhanced matrix penetration. With the mixed coculture technique (FIG. 22), there was no evidence of cell sorting, although matrix penetrance by the smooth muscle cells was evident.

It was also established that there are SMC/UC interactions that are involved in the determination of the type of growth seen on the membrane (proliferative vs. differentiative, invasive vs. surface limited), and that it is necessary for the cells to be in physical contact with each other to achieve the most "tissue-like" appearance in culture. The presence of urothelial cells significantly impacts the pattern of smooth muscle cell growth on small intestinal submucosa since active penetrance of the membrane only occurs when urothelial cells are grown in conjunction with smooth muscle cells.

To assess the effect of cell density on graft development, the seeding density of the SMC and UC on the SIS membrane was varied and cultured for the period previously shown to yield optimum histological organization. After 14 days of culture, the grafts were harvested for comparative histology. It was determined that while the higher seeding density yielded a thicker layer of cells on the surface of the membrane (1-2 layers more cells), that invasion into the interstices of the membrane by SMCs was significantly enhanced in the $10^5$ cells/cm$^2$ cultures. The lowest seeding density had a paucity of cells which were limited to the surface of the membrane with no evidence of invasion. We feel that a compelling case can be made for using the culture parameters outlined to create our material for re-implantation into the animal. First, using a medium density seeding allows us to generate enough cells to do the procedure in a shorter period of time. Second, the medium density cultures have a more tenacious hold on the membrane and are less likely to be abraided from the graft due to manipulation during the re-implantation process, thereby leaving more cells to participate in the regenerative process. Finally, with the medium density cell inoculum, the process of tissue reorganization has already begun to occur in culture. Thus, the graft is further along in the regenerative process and this should lead to a faster regeneration of functional bladder tissue in the host animal.

In summary, the best method of seeding was achieved by first seeding the mucosal surface of the graft with smooth muscle cells followed by urothelial cells one hour later. The optimal seeding density was 100,000 cells/cm$^2$. This seeding method yielded a seeded graft that had the best histologic characteristics relative to normal bladder. There was a well developed pseudostratified urothelium with multiple layers of smooth muscle cells proliferating within the matrix of the SIS membrane. Additionally, it was determined that after 14 days in culture, the seeded graft does not further mature and differentiate when carried out to 28 days.

Once the coculture conditions were optimized using the small intestinal submucosa disks, such coculture conditions were applied to a large-scale study in which 7×10 cm segments of small intestinal submucosa were suspended in the two tissue culture frames described herein above, and dog bladder smooth muscle and urothelial cells were seeded thereon by the layered coculture method described above. Both of the tissue culture frames are user-friendly and easy to clean, sterilize and store and do not affect cell growth or differentiation.

Figure 23:
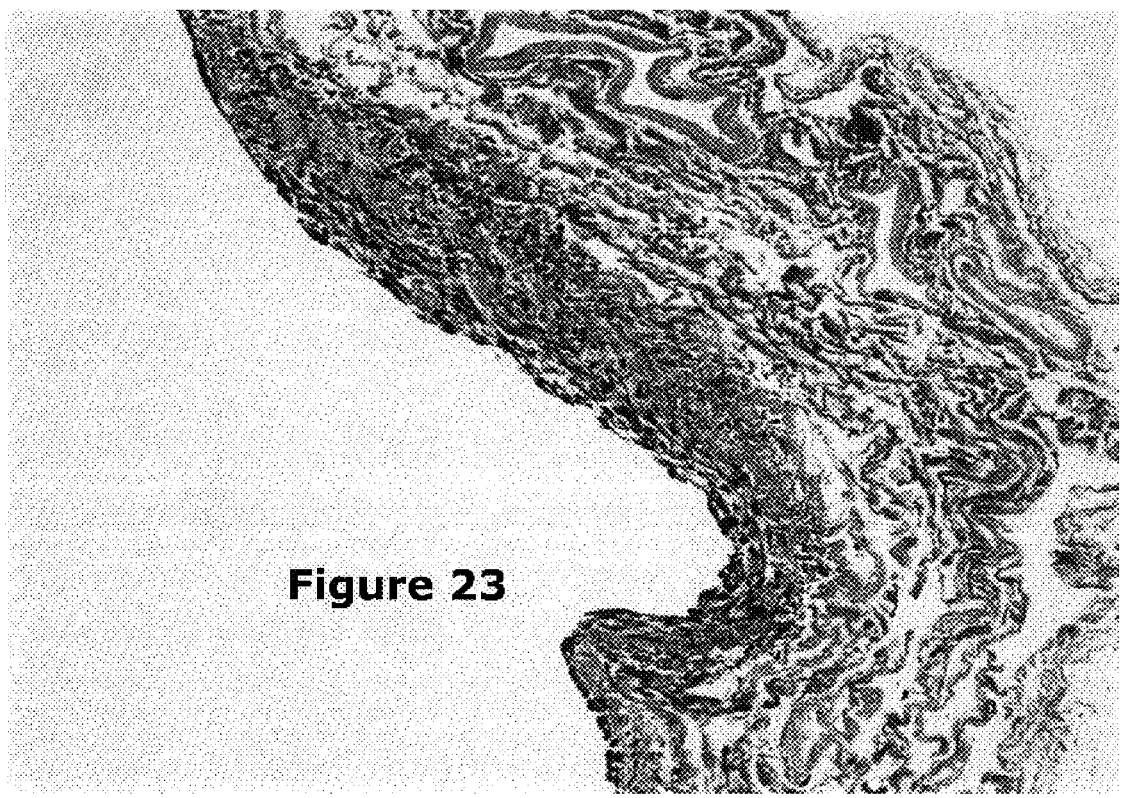
FIG. 23 is a photomicrograph illustrating layered coculture of dog bladder epithelial and smooth muscle cells on small intestinal submucosa membrane before implanting of graft. At 14 days there are several areas where smooth muscle cells traverse deep into small intestinal submucosa membrane and epithelial cells grow on the top of smooth muscle cells (Masson Trichrome staining x 20).

On day 14, the urothelial cells were flattened in shape and grew on top of the smooth muscle cells, which were spindle shaped. Distinct cell sorting was noted in which the smooth muscle cells grew on top of the SIS with early matrix penetrance, while the urothelial cells grew on top of the smooth muscle cells as a separate population of cells. The SMC layer was up to 5-7 layers thick. The vast majority of SMC were no longer on the surface of the SIS. Rather, they had penetrated the matrix of the SIS membrane and were now proliferating under the surface of the SIS within the membrane. In several areas, SMC could be seen traversing into the deep portions of the SIS membrane (FIG. 23).

Figure 24:
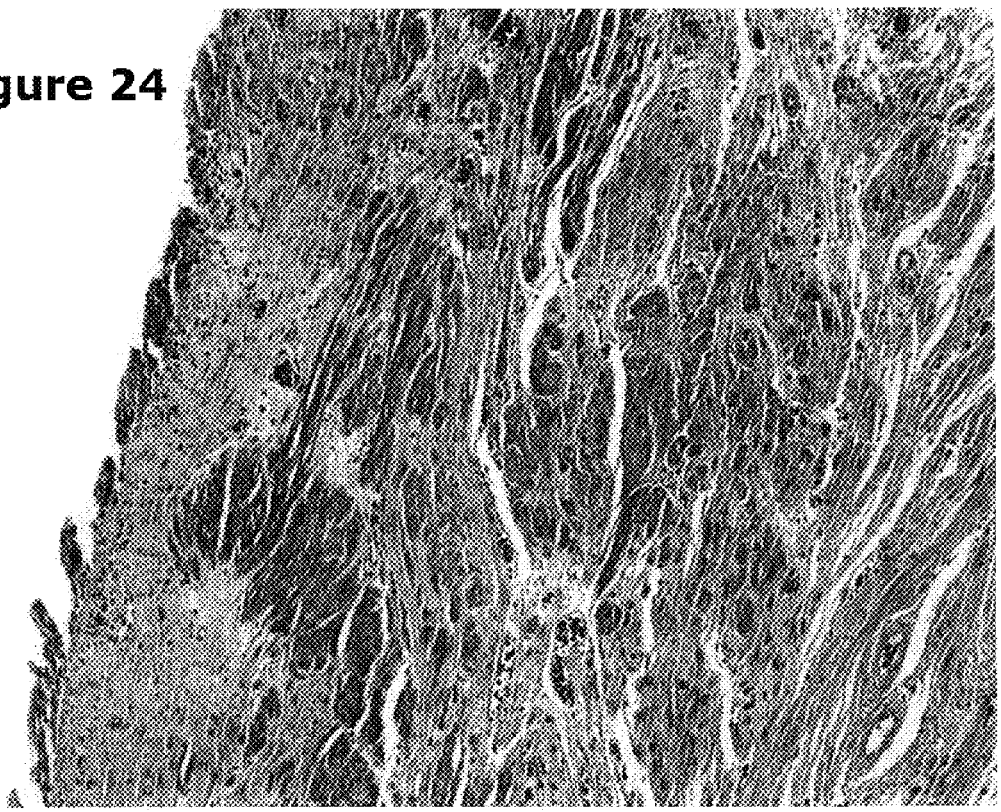
FIG. 24 is a photomicrograph of Masson trichrome stained cell-seeded small intestinal submucosa regenerated dog bladder at 10 weeks postaugmentation. All layers of bladder are present. Abundant smooth muscle bundle formations (red) are surrounded by collagenous matrix (blue) X 20.

Ten weeks after augmentation, the cell-seeded grafts had grossly minimal adhesions to the surrounding perivesical fat or other intra-abdominal structures. Histologically, the SIS grafts were completely covered by urothelial cells. Grafts showed a prominent neovascularization at their edges and infiltration of their entire surface by the new capillaries. Regenerated smooth muscle bundle formation was present and indistinguishable from the normal native bladder (FIG. 24).

Thus it should be apparent that there has been provided in accordance with the present invention a urinary tract tissue graft composition, a method of providing a urinary tract tissue graft composition, and a method for repairing a damaged urinary tract tissue of a subject, that fully satisfies the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

What is claimed is:

1. A urinary tract tissue graft composition, consisting essentially of a distal ileal segment of small intestinal submucosa isolated from a mature adult pig.

2. A bladder tissue graft composition, consisting essentially of a distal ileal segment of small intestinal submucosa isolated from a mature adult pig.

3. A kit, comprising:
 means for suspending a segment of small intestinal submucosa in a taut position; and
 an isolated distal ileal segment of small intestinal submucosa suspended on said means in a taut position such that cells may be seeded thereon.

4. The kit of claim 3 wherein the distal ileal segment of small intestinal submucosa has been isolated from a mature adult pig.

5. A kit, comprising:
 a tissue culture frame for suspending a segment of small intestinal submucosa in a taut position; and
 an isolated distal ileal segment of small intestinal submucosa suspended in the tissue culture frame and held taut such that cells may be seeded thereon.

6. The kit of claim 5 wherein the distal ileal segment of small intestinal submucosa has been isolated from a mature adult pig.

* * * * *

UNITED STATES PATENT AND TRADEMARK OFFICE
CERTIFICATE OF CORRECTION

PATENT NO. : 7,507,422 B2  Page 1 of 1
APPLICATION NO. : 11/326533
DATED : March 24, 2009
INVENTOR(S) : Kropp et al.

It is certified that error appears in the above-identified patent and that said Letters Patent is hereby corrected as shown below:

Column 1, lines 22-27: Delete entirety of paragraph and replace with -- This invention was made with government support under Grant No. DK056968 awarded by the National Institutes of Health. The government has certain rights in the invention. --

Signed and Sealed this

Sixteenth Day of March, 2010

David J. Kappos
*Director of the United States Patent and Trademark Office*